United States Patent
Uddin

(10) Patent No.: US 11,110,072 B2
(45) Date of Patent: Sep. 7, 2021

(54) BROAD SPECTRUM PHARMACOLOGICAL COMPOSITION FOR TREATMENT OF VARIOUS INFECTIONS AND DISEASES AND METHODS OF USE

(71) Applicant: Naeem Uddin, Karachi (PK)

(72) Inventor: Naeem Uddin, Karachi (PK)

(73) Assignee: Greyfer Innova Pharma, LLC, Karachi (PK)

( * ) Notice: Subject to any disclaimer, the term of this patent is extended or adjusted under 35 U.S.C. 154(b) by 0 days.

(21) Appl. No.: 17/178,351

(22) Filed: Feb. 18, 2021

(65) Prior Publication Data

US 2021/0177788 A1 Jun. 17, 2021

Related U.S. Application Data

(63) Continuation-in-part of application No. 16/838,141, filed on Apr. 2, 2020, now Pat. No. 10,925,847, which is a continuation of application No. 16/688,094, filed on Nov. 19, 2019, now Pat. No. 10,646,461, which is a continuation-in-part of application No. 15/891,839, filed on Feb. 8, 2018, now Pat. No. 10,493,050, which is a continuation-in-part of application No. 15/062,156, filed on Mar. 6, 2016, now Pat. No. 9,962,347, which is a continuation-in-part of application No. 13/913,555, filed on Jun. 10, 2013, now Pat. No. 9,301,935.

(51) Int. Cl.

| | | |
|---|---|---|
| *A61K 31/194* | (2006.01) | |
| *A61P 33/14* | (2006.01) | |
| *A61K 9/00* | (2006.01) | |
| *A61K 31/573* | (2006.01) | |
| *A61K 31/192* | (2006.01) | |
| *A61K 9/107* | (2006.01) | |
| *A61K 31/60* | (2006.01) | |
| *A61K 47/44* | (2017.01) | |
| *A61P 17/14* | (2006.01) | |
| *A61P 33/02* | (2006.01) | |
| *A61P 31/04* | (2006.01) | |

(52) U.S. Cl.
CPC .......... *A61K 31/194* (2013.01); *A61K 9/0014* (2013.01); *A61K 9/107* (2013.01); *A61K 31/192* (2013.01); *A61K 31/573* (2013.01); *A61K 31/60* (2013.01); *A61K 47/44* (2013.01); *A61P 33/14* (2018.01); *A61P 17/14* (2018.01); *A61P 31/04* (2018.01); *A61P 33/02* (2018.01)

(58) Field of Classification Search
CPC ..... A61K 9/0014; A61K 31/194; A61P 33/14; C07C 55/06; C07C 55/07
See application file for complete search history.

(56) References Cited

U.S. PATENT DOCUMENTS

| | | |
|---|---|---|
| 5,639,459 A | 6/1997 | Bouras |
| 5,648,389 A | 7/1997 | Gans |
| 6,407,141 B1 | 6/2002 | Hart |
| 6,936,579 B2 | 8/2005 | Urban |
| 6,982,097 B2 | 1/2006 | Mingzhang et al. |
| 7,517,842 B2 | 4/2009 | Barnhart et al. |
| 7,618,658 B2 | 11/2009 | Tsuchida et al. |
| 7,883,715 B2 | 2/2011 | Abraham et al. |
| 2007/0027119 A1 | 2/2007 | Ahmed et al. |
| 2007/0184016 A1 | 8/2007 | Macinga et al. |
| 2010/0234460 A1 | 9/2010 | Foret et al. |
| 2010/0292333 A1 | 11/2010 | Mladenovich |
| 2011/0152384 A1 | 6/2011 | Gunn et al. |
| 2012/0015809 A1 | 1/2012 | He et al. |
| 2012/0269751 A1 | 10/2012 | Stal |
| 2012/0302642 A1 | 11/2012 | Post |

OTHER PUBLICATIONS

Sigmundsdottir, Trends in Pharmacological Sciences 31 (2010) 239-245.
R. Von Burg, Journal of Applied Toxicology, vol. 14(3), 233-237 (994).
Nagaoka et al (Letters in Applied Microbiology 51, 546-551).
Drugs (https://web.archive.org/web/20130221134540/https://www.drugs.com/pro/sodium-citrate-and-citric-acid-oral-solution.html, published Feb. 2013) (Year: 2013) Cannot locate. in U.S. Pat. No. 9,962,347 in lineage.

*Primary Examiner* — Theodore R. Howell
(74) *Attorney, Agent, or Firm* — Michael E. Zall

(57) ABSTRACT

A pharmacological composition for the treatment of bacterial and protozoal infections in a patient. The preferred pharmacological composition comprises a pharmaceutical carrier and an active composition selected from the group consisting of: a) an amount of sodium oxalate and an amount of oxalic acid, b) an amount of sodium citrate and an amount of citric acid, or c) mixtures of a) and b). The amounts and weight ratios of a) the sodium oxalate and oxalic acid, and b) the sodium citrate and citric acid in the active composition are such as to produce a safe and effective pharmacological composition. Sodium salts of other carboxylic acids may be used. The invention also relates to the method of using the pharmacological composition for the safe and effective treatment of bacterial infections, protozoal infections, lice and dermatological diseases.

10 Claims, No Drawings

BROAD SPECTRUM PHARMACOLOGICAL COMPOSITION FOR TREATMENT OF VARIOUS INFECTIONS AND DISEASES AND METHODS OF USE

RELATED APPLICATIONS

This application (CIP-4) is a continuation-in-part application of U.S. application Ser. No. 16/838,141 filed on Apr. 2, 2020 (Comp), now U.S. Pat. No. 10,925,847 issued on Feb. 23, 2021, which is a continuation of U.S. application Ser. No. 16/688,094 filed on Nov. 19, 2019 (CIP-3), now U.S. Pat. No. 10,646,461 issued on May 12, 2020, which is a continuation-in-part application of U.S. application Ser. No. 15/891,839 filed on Feb. 8, 2018 now U.S. Pat. No. 10,493,050 issued on Dec. 3, 2019 (CIP-2), which is a continuation in part of U.S. application Ser. No. 15/062,156 filed on Mar. 6, 2016, now U.S. Pat. No. 9,962,347, issued on May 8, 2018 (CIP-1), which is a continuation in part of U.S. application Ser. No. 13/913,555 filed on Jun. 10, 2013, now U.S. Pat. No. 9,301,935 issued on Apr. 5, 2016 (Parent), the entire disclosures of all of these patents and applications are incorporated herein by reference.

BACKGROUND OF THE INVENTION

Field of the Invention

The present invention relates to a pharmacological composition that is a safe and effective broad spectrum antibiotic, particularly against gram positive and gram negative bacteria, anti-protozoal, and can be used for the treatment of various diseases and for the treatment of various dermatological disorders in patients. In particular, the composition of this invention, inhibits the growth or destroys the bacteria, and inhibits or destroys protozoal infections. In particular the composition of this invention ameliorates, prevents and/or treats bacterial infectious diseases. The active ingredients in the preferred pharmacological composition are a) a mixture of sodium citrate and citric acid, and/or b) a mixture of sodium oxalate and oxalic acid. However, similar mixtures of the active cation of sodium salts with anions of organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof. The compositions of this invention may be administered orally.

Related Art

Applicant is aware of the following references that may be relevant to this invention:

US Published Application 2007/0027119 to Ahmed et al. describes a nonirritating antimicrobial liquid composition with citric acid and oxalic acid combination and alcohol used in skin treatment, primarily a teat treatment for cows.

US Published Application 2007/0184016 to Macinga et al. describes a pre-surgical disinfectant with alcohol and citric acid, oxalic acid or mixtures thereof.

US Published Application 2010/0234460 to Foret et al. describes disinfectant solution for the treatment of hoof diseases that contains a surfactant and one or more carboxylic acids, e.g., citric acid and oxalic acid.

US Published Application 2010/0292333 to Mladenovich describes fungal infection treatment composed of two or more low-molecular weight organic acids, e.g., oxalic acid and citric acid, and their salts.

US Published Application 2011/0152384 to Gunn et al. describes skin care composition with emulsifier and organic acids, including oxalic acid or citric acid.

US Published Application 2012/0015809 to He et al. describes a surface cleaner with formic acid and an enhancing component of citric acid that may be mixed with oxalic acid for the control of pests, including fungi, oomycetes, nematodes and weeds.

US Published Application 2012/0269751 to Stal describes a topical composition of physiologically acceptable carboxylic acid such as citric acid and/or oxalic acid for the treatment of skin and nail conditions, i.e., microbiological infections of the nail (onychomycosis), warts.

US Published Application 2012/0302642 to Post abrasive acidic cleaning composition for hard surfaces, e.g., lavatory surfaces, which includes a colloid forming clay, a thickener, a surfactant and antimicrobial amounts of an organic acid and an abrasive constituent. The organic acid may be a citric acid, oxalic acid or mixtures thereof.

U.S. Pat. No. 5,639,459 to Bouras describes a composition to treat hair loss, baldness and alopecia that embodies using oxalates, e.g., ammonium oxalate meta. The use of citric acid is in conjunction therewith is taught. The treatment " . . . enhances the aesthetic appearance of scalp and skin."

U.S. Pat. No. 5,648,389 to Gans et al. describes a topical treatment for dermatological disorders using zinc compound and ahydroxy acid that may be citric acid and the zinc compound may be zinc oxalate.

U.S. Pat. No. 6,114,389 to Bouras describes a method for treating diseases of the skin by applying a pharmaceutically acceptable oxalate, e.g., a metal oxalate in an ointment.

U.S. Pat. No. 6,407,141 to Hart describes hemo-therapeutic chemo-preventative composition for treating vascular diseases that contains oxalic acid and/or oxalate.

U.S. Pat. No. 6,936,579 to Urban describes a hard surface cleaning composition with citric acid and oxalic acid.

U.S. Pat. No. 6,982,097 to Mingzhong et al. describes a biocide composition for disinfecting water that includes a filler of sodium citrate, oxalic acid, sodium bromide, and a halogen releasing compound.

U.S. Pat. No. 7,517,842 to Barnhart et al. describes an antimicrobial hand wash formulation with a cationic surfactant produced from the neutralization of an amid amine with an acid and an active ingredient. The acid may be an oxalic acid or citric acid as the acid neutralizer.

U.S. Pat. No. 7,618,658 to Tsuchida et al. describes an antimicrobial composition of Sasaextract and the use of citric acid or oxalic acid to improve the antimicrobial activity.

U.S. Pat. No. 7,883,715 to Abraham et al. describes enhancing the herbicidal effectiveness of glyphosate through the addition of a dicarboxylic acid, in particular oxalic acid.

Citric Acid

Citric acid is well known. Citric acid was first isolated in 1784 by the chemist Wilhelm Scheele, who crystallized it from lemon juice. Industrial-scale citric acid production first began in 1890. In 1893, C. Wehmer discovered penicillium mold could produce citric acid. In 1917, American food chemist James Currie discovered certain strains of the mold *Aspergillus niger* could be efficient citric acid producer.

Citric Acid, 2-hydroxytricarboxylic acid is of biological origin and its functionality makes it suitable for wide range of application. The presence of one hydroxyl group and 3 carboxyl groups permits the formation of complex molecules, which may be soluble and capable of modifying the solubility of constituent's material. Citric acids, Oxalic acid, along with lactic acid, acidulant and its salts are preferred buffers in pharmaceutical preparation. Citric acid crystallizes from a cold aqueous solution as monohydrate (C6H8O7H2O). The crystal is color less. It is optically inactive. Citric acid is strong organic acid as indicated by the first dissociation constant which is $8.2 \times 10^4$ at 18 degree Celsius. The second and third dissociation constants are $1.77 \times 10^{-4}$ and $3.9 \times 10^{-7}$ respectively. Citric acid is readily soluble in water and in various organic compounds.

Citric acid is a natural preservative present in citrus fruits. It is white hygroscopic crystalline powder. It can exist either in an anhydrous (water-free) form or as monohydrate. Citric acid also dissolves in absolute (anhydrous) ethanol. It is also used to add an acidic or sour taste to foods and drinks and is used mainly as acidifier, flavoring and chelating agent.

The FDA lists citric acid in the Nov. 20, 1959 issue of the federal register (23-a) as a substance that is generally recognized as safe for specific use in compliance with the Food additive amendment of 1958. Even at high concentrations citric acid is not injurious in contact with skin.

After oral administration of citric acid the citrate ion is rapidly and almost completely oxidized, less than 1% being excreted unchanged in urine. Intravenous injection shortens, coagulation times of the blood but in vitro, the citrate ion acts as an anticoagulant.

With sodium bicarbonate, citric acid is used in many effervescent powder and tablets to liberate carbon dioxide when added to water. Citric acid salt's such as sodium citrate and potassium citrate and citric acid are also used in different remedies like in CITRO-SODA® (Abbott Laboratories) which is characterized as a gastric antacid and urinary alkalinizing agent.

Sodium Citrate

Sodium Citrates are used as acidity regulators in food and drinks, and also as emulsifiers for oils, e.g., with citric acid it is used as a buffering agent for controlling PH in the preparation of candies In pharmaceutical preparations, such as effervescent tablets, powders and droughts, sodium citrate is used as blood and urinary alkalizer and in large dosages as a saline cathartic. Due to its anticoagulant property of citrate ion, sodium citrate is extensively employed for this purpose. And the final product is known officially in US Pharmacopeia as citrated, normal human plasma when blood is drawn from an individual under aseptic condition into sterile bottle. Such bottle contains 50 ml of a 4% solution of sodium citrate in isotonic sodium chloride solution. To this is added 50 ml of whole blood. Sodium Citrate prevents blood from coagulation.

OBJECTS AND SUMMARY OF THE INVENTION

The present invention is directed to a pharmacological composition for the treatment of bacterial and protozoal infections in a patient. The pharmacological composition comprises a pharmaceutical carrier and an active composition selected from the group consisting of an amount of an active cation sodium salt with an anion organic acid and an amount of the organic. The organic acid is selected from the group consisting of citric acid, oxalic acids, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid or combinations thereof. The amounts and weight ratios of such amounts in the active composition result in a safe and effective pharmacological composition.

The preferred pharmacological composition comprises a pharmaceutical carrier and an active composition selected from the group consisting of:
 a. an amount of sodium oxalate and an amount of oxalic acid,
 b. an amount of sodium citrate and an amount of citric acid, or
 c. mixtures of a. and b, The amounts and weight ratios of a) the sodium oxalate and oxalic acid, and b) the sodium citrate and citric acid in the active composition are such as to produce a safe and effective pharmacological composition.

The invention also relates to the method of using the pharmacological composition for the safe and effective treatment of bacterial infections, protozoal infections and dermatological diseases.

DETAILED DESCRIPTION OF THE INVENTION

Unless specified otherwise, all ingredients are in weight/weight percent (w/w %), i.e., the weight of the ingredient relative to the weight of the final composition described as a percentage.

A "therapeutically effective amount" means the amount of the pharmacological composition described herein that will disinfect, inactivate or significantly diminish the population of a microorganism or protozoa, or effectively treat a given disease or condition, e.g., bacterial infection, protozoal infection, or dermatological diseases or infections.

Preferred Active Composition: Sodium Oxalate and Oxalic Acid

The theoretical stoichiometric ratio of oxalic acid and sodium bicarbonate for the preparation of sodium oxalate is 1:1.33 weight ratios. Theoretically this produces 100% sodium oxalate.

The active composition used in the pharmacological compositions of this invention uses a 1:1 weight ratio of oxalic acid to sodium bicarbonate to make the active composition. This produces a final active composition with an excess of oxalic acid mixed with sodium oxalate. This imparts a safe and efficacious medicinal activity to the composition. The active composition maintains a pH of about 6 which acceptable for patient use.

The highly preferred composition is a mixture of 78.44% sodium oxalate and 21.56% oxalic acid. A preferred range is about 73% to about 83% Sodium oxalate and about 17% to about 27% oxalic acid. It is to be understood however that various weights and ratios of sodium oxalate and oxalic acid may be used as long as a safe and efficacious pharmacological composition is produced.

Sodium Oxalate—Oxalic Acid Mixture a) Stoichiometric Formulation Ratio:

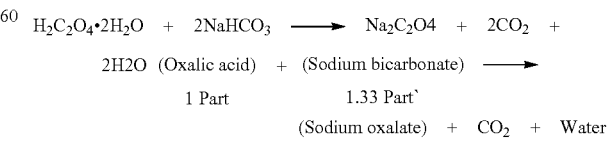

b) Method of Producing Active Composition:

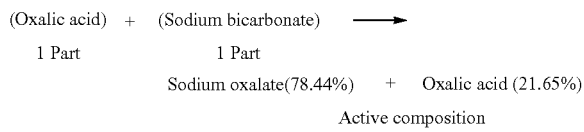

Method of Preparation of Mixture of Sodium Oxalate—Oxalic Acid as Active Ingredient Mix one part oxalic acid and one part sodium bicarbonate than gradually spray sterile water into the mixture to make reaction. The water is merely the medium for the reaction. Carbon dioxide is evaporated rapidly and water is gradually evaporated. The remaining product is a mixture of 78.44% Sodium Oxalate and 21.56% Oxalic acid active ingredient. The product is in the form of crystals. The product is then dried and crushed to fine particles to produce an active composition suitable for formulation into the pharmacological formulations of this invention.

Preferred Active Composition: Sodium Citrate and Citric Acid

The theoretical stoichiometric ratio of citric acid and sodium bicarbonate for the preparation of sodium oxalate is 1:1.2 weight ratios. Theoretically this produces 100% sodium citrate. The active composition used in the pharmacological compositions of this invention uses a 1:1 weight ratio of citric acid to sodium bicarbonate to make the active composition. This produces a final active composition with an excess of citric acid mixed with sodium citrate. This imparts a safe and efficacious medicinal activity to the composition. The active composition maintains a pH of about 6 which acceptable for patient use.

The highly preferred composition is a mixture of 87% sodium citrate and 13% citric acid. A preferred range is about 82% to about 92% Sodium citrate and about 8% to about 18% citric acid. It is to be understood however that various weights and ratios of sodium citrate and citric acid may be used as long as a safe and efficacious pharmacological composition is produced.

Sodium Citrate—Citric Acid Mixture
a) Stoichiometric Formulation Ratio:

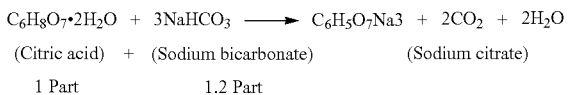

b) Method of Producing Active Composition:

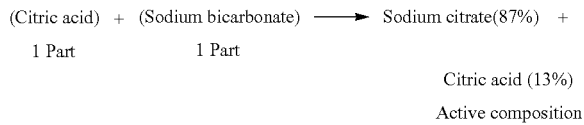

Method of Preparation of Mixture of Sodium Citrate—Citric Acid as Active Ingredient Mix one part citric acid and one part sodium bicarbonate than gradually spray sterile water into the mixture to make reaction. The water is merely the medium for the reaction. Carbon dioxide is evaporated rapidly and water is gradually evaporated. The remaining product is a mixture of 87% Sodium citrate and 13% citric acid active ingredient. The product is in the form of crystals. The product is then dried and crushed to fine particles to produce an active composition suitable for formulation into the pharmacological formulations of this invention.

Similar mixtures of sodium salts and organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof.

The pharmacological compositions of this invention include a pharmaceutically acceptable carrier that does not adversely affect the efficacy and safety of the compositions. The carrier is highly dependent on the selected modality of treatment. For example, the pharmacological compositions may be orally administered, topically applied, administered as a suppository, and as an injectable. The carrier may include, for example, an additive selected from a buffering agent, an emollient, a humectant, a preservative, a surfactant or wetting agent, a viscosity control agent, a colorant, an opacifying agent, and any combinations thereof.

The pharmacological composition may also include additional suitable components, for instance fragrances, emulsifiers, detergents, antioxidants and preservatives, and other ingredients commonly used in pharmaceutical and cosmetic formulations. Preferably, the composition is essentially free of water, which increases the stability of the composition over time. Preferably, the composition is formulated as a fluid composition such as a cream, or more preferably as a liquid composition, which is relatively easy to apply to the human skin and/or nails.

Methods of preparing the pharmacological compositions may involve dissolving a desired concentration of the active composition and, alternatively, any desired additives in a selected pharmaceutical carrier. The solution is then mixed, for example in a mixer, to form a final pharmacological composition. Useful concentrations are those where the percentage of the active composition by total weight of the composition is preferably from about 0.02 to 20% by weight of the pharmacological composition. The pharmaceutical carrier may be present from 80 to 99.98% by weight. More preferably, this is from about 0.03 to 15% of each active composition and from about 85% to 99.97% of a pharmaceutical carrier.

The phrase "therapeutically effective amount" is intended to qualify the amount of the pharmacological composition which will achieve the goal of the composition, e.g., reduction of bacteria, reduction of protozoal activity, and treatment of dermatological diseases. "Therapeutically effective" may also refer to improvement in disorder severity or the frequency of incidence over no treatment.

The term "topical" and "locally" application shall refer to any composition applied on skin, eye, auditory canal, oral mucosa and in vaginal mucosa where the application of my invention is indicated.

Broadly, the pharmacological composition of this invention is used for the treatment of bacterial and protozoal infections in a patient and treating a dermatological disease in a patient.

The pharmacological compositions of this invention may also contain water and a "structuring agent" such as carbomers or other thickening polymers, for example, xanthan gum, carrageenan gum or the like. The compositions may be made into a wide variety of product types that include but are not limited to lotions, sprays, wipes, and make-up such as foundations. These product types may comprise several types of cosmetically-acceptable topical carriers. Preferably the carrier is alcohol free.

Preferred carriers for the active composition, based on the foregoing criteria for use, are:
Preferred Carrier Compositions (by Weight):
 1) 20% emulsifying wax, 10% Liquid paraffin and 70% water.
 2) 20% emulsifying wax and 80% water.
 3) 2% carboxymethyl cellulose and 98% water.

Antibiotic

More specifically the pharmacological compositions are used as a broad spectrum antibiotic. Preferably, the mixture of sodium oxalate and oxalic acid is used alone as the active composition, as is the mixture of sodium citrate and citric acid. A mixture of these active compositions may also be used.

The pharmacological composition of this invention may be used orally, topically in the form of ointment, cream, and drops (for eye and ear) through suppository and parentally by injection, infusion or implantation. The pharmacological compositions of this invention are effective against gram positive and gram negative bacteria, for example: *Staphylococcus aureus, Epidermidis, Streptococcus Aagalactae, E. coli, Klebsilla, Proteus, Entrobacter, Entrococcous, Citrobacter, Propionibacterium* acne, *Corynebacterium*, B. *Subtilis*, and *Serratia* but not limited to these.

The pharmacological composition of this invention may be used where antibiotics are indicated in the treatment of infections caused by pathogens sensitive to it, for example in pneumonia, chronic bronchitis, acute exacerbation of chronic bronchitis, community acquired pneumonia, sinusitis otitis media, urinary tract infection, genital tract gonococci urethritis, non gonococci urethritis, cervicitis, skin and soft tissue infections, chalazion, conjunctivitis, otitis externa, otitis media tympanits, perotinitis, cholecystis, appendicitis, folliculitis, paronychia, carbuncle and other such infections.

Protozoa

The pharmacological compositions of this invention may be used for reducing protozoa in a patient having a protozoal infection, i.e., an anti-protozoal composition. The composition acts against trichomonads which causes trichomoniasis. It also acts against antamoeba histolytica, causes amaebiasis and Giardia, causes Giardiasis the gastroenteritis intestinalis. Some other protozoa are human parasites, causing diseases. Examples of diseases caused by protozoa, which the compositions of this invention are effective against, are Malaria, Amoebiasis, Giardiasis, Toxoplasmosis, Cryptosporidiosis, Trichomoniasis, Chagas disease, Leishmaniasis, Sleeping Sickness, and Dysentery.

Dermatological Diseases

The pharmacological compositions of this invention may be used for treating dermatological diseases in a patient having such a disease. Preferably, the mixture of sodium oxalate and oxalic acid is used alone as the active composition, as may the mixture of sodium citrate and citric acid. A preferred dermatological pharmacological composition of this invention for the treatment of skin diseases includes about 1% to about 10% of the sodium oxalate and oxalic acid mixture as the active composition or about 1% to about 10% of the sodium citrate and citric acid as the active composition. Optionally, about 1% to about 4% Salicylic acid, steroid (colobetasol, hydrocortisone), Benzoic acid and zinc oxide may be added to enhance the effect of composition. For dry skin, an oily base may be used. For an oily skin, a water base may be used. If the pharmacological composition needs to be taken orally, a nontoxic (edible) water based carrier should be used. If the pharmacological composition is for vaginal use a water or oil base carrier should be used.

Hyperhidrosis

The pharmacological compositions of this invention may also be used for treating hyperhidrosis. Hyperhidrosis is a disease of excessive production of sweat, particularly from the palms, soles and axillae. Hyperhidrosis may be due to pharmacologically acting agents acting on the sweat glands, abnormal stimulation of the sympathetic path-ways between the hypothalamus and nerve endings or over activity of one of three different centers responsible for thermoregulatory, mental and gustatory centers or of unknown cases.

Whatever the underlying cause of hyperhidrosis, the pharmacological compositions of this invention act locally to suppress and/or cure hyperhidrosis by developing anhidrotic areas by directly acting on the sweat glands (eccrine and apocrine glands).

The preferred treatment is with a topical pharmacological composition having 2% to 10% (by weight) of a mixture of sodium citrate and citric acid or, alternatively with a 2% to 10% mixture of sodium oxalate and oxalic acid.

Lice

The pharmacological compositions of this invention may also be used for treating lice. This is accomplished by the direct interference by the compositions of this invention with the respiratory function of the lice by blocking the spiracles of the lice. This is accomplished without any adverse effect on the skin, and particularly to children that would use the composition.

Lice are members of phthiraptera. They spend their entire life on the host, e.g., animals or people. Man is parasitized by two species. Two species are from the sub-order anoplura, and are the *Pediculushumanus* and *Pithrus pubis* species. There are two species of *Pediculus humanus*; they are *P humanus capitis* (head lice) and *P humanus humanus* (body or clothing lice). *Pithirus pubis* (pubic or crab lice) is morphologically quite distinct from *Pediculus humanus*. Infection with pubic lice is termed pithiriasis while infection with *Pediculus humanus* is termed Pediculosis.

The pharmacological compositions of this invention produce a multi action affect to eradicate the lice. It is a pediculicider and an ovicider. Eggs of head lice, and empty egg cases are cemented to hair shaft with a chitinous cement material secreted by the female accessory glands and are difficult to dislodge. The pharmacological compositions of this invention dissolve chitinous material to loosen the eggs so that they can be removed by combing the hair. The pharmacological compositions also have antihydrotic effect and create anhidrotic area in scalp which creates an unfavorable environment for lice development. The compositions when applied locally will kill the lice within 24 hours.

The preferred treatment is with topical pharmacological compositions of a 2% to 10% (by weight) of a mixture of sodium citrate and citric acid or, alternatively with a 2% to 10% mixture of sodium oxalate and oxalic acid.

More specifically, this invention is directed to the treatment of lice occurring on mammals, e.g., humans and animals including cows, buffalos, goats and birds. Lice are members of the order Phthiraptera. They are wingless, dorsoventrally flattened insects which are obligate ectoparasites of mammals and birds.

Lice are members of order Phthiraptera. Phthiraptera are highly host specific and spend their entire life on the host. Humans are parasitized by two species of the sub-order Anapleura:
   a. *Pediculus Humanus*
   b. *Pthirus Pubis*.

There are two sub-species of *Pediculus Humanus:*
   a. *Pediculus Humanus* Capitis (head lice)
   b. *Pediculus Humanus Humanus* (body or clothing lice).

Head lice and body lice are morphologically almost identical and are capable of interbreeding while *Pthirus Pubis* (the pubic or crabs lice) are morphologically quite distinct from *Pediculus Humanus*. Infection with pubic lice is termed Phthiriasis Morphology and Biology of Lice:
   a. *Pediculus Humanus*: The adult female is grayish white, 3-4 mm long. The male is slightly smaller. The claws on the legs are adapted for clinging to hair. During its span of life of approximately 40 days, the female is capable of creating about 300 eggs at the rate of 7-10 daily. The eggs of head lice are cemented to the hair shaft with a chitinous cement material secreted by the female accessory glands. Eggs hatch in about 8 days and following 3 moults the louse nymph reaches maturity in about 10 days.
   b. *Pediculus humanus humanus*: Body lice are almost identical in appearance to head loice and develop in same manner as *Pediculus humanus*. Their natural habitat, is the clothing of the host and they only visit the skin to feed. The eggs are cemented with chitinous material secreted by accessory glands of the female to clothing fibers, the favored sites.
   c. *Pthirus Pubis*: Pubic or crab lice are distinct in appearance and habits from *Pediculus* lice. Its body is squared, second and third pairs of legs carry pincer like claws. The eggs are light brown in color. Crab lice colonize axillary hairs, eye borrows, eye lashes, beard and hair on the trunk and limbs.

The vast majority of head lice infestations are acquired by direct head to head contact. Generally, lice infestations are created by poor hygiene and overcrowding. Crab lice are transmitted by close physical contact, usually during sexual contacts between individuals. The typical symptom of a lice infestation is itching, typically in the evening and at night.

Mode of Action of Treatment of this Invention
   1. The composition used in the method of this invention interferes with respiratory function of the lice by blocking the spiracles (opening through which lice breathe).
   2. The composition used in the method of this invention acts as an ovicidal, i.e., the nymph eggs are prevented from hatching.
   3. The lice eggs are cemented to hair shafts with a chitinous cement material secreted by the females accessory glands. The composition used in the method of this invention loosens and liquefies the chitinous material to separate the attached eggs and nits (empty eggs) from the hair.

In summary, lice infestation occurs under the following circumstances:
   a. Unhygienic conditions wherein the patient does not comb and/or wash his/her hair on a regular basis.
   b. In close gathering for, e.g., schools, dorms, hostels, etc. where people, particularly children, are gathered and seated together.
   c. Family gatherings, if one person is affected and comes in contact with other family members, the other members also develop lice, and in this way it is spreaded person to person by body contact and cloth contact and share sleeping on same bed.
   d. Incidence also increases in neglected persons either he or she living alone or in family but not being cared by family members or society.
   e. Incidences of lice are higher in addictive person using recreational drugs.
   f. It is also common in mentally retarded and homeless persons.
   g. The disease also spreaded in contagious places where the towels, soaps are commonly used.

The method of this invention is safe and effective and without having any serious side effects. This treatment method is also low in cost, the pharmacological compositions are simple to manufacture for the treatment of a lice infection and to ameliorate, prevent and/or treat lice.

The method of this invention for treating a lice infection comprises topically administering a pharmacological composition, comprising a sodium oxalate and oxalic acid mixture with specific ratio by weight and percentage. The composition can be applied topically to mammals and birds. A composition (topical composition) for treating above mentioned conditions may comprise a sodium oxalate and oxalic acid mixture with a specific stoichiometric ratio specifically 5% by weight and 0.025% by weight $KMnO_4$ (Potassium Permanganate) incorporated in a prepared vehicle mentioned above.

Method of Administration

The method of administration of the pharmacological composition is to apply it locally to the patient/animal. The therapeutically effective amount of the composition is an amount that will ameliorate or prevent the disease, i.e., lice infection. The pharmacological composition of this invention should not contact the eyes or open wounds.

Scabies

The pharmacological compositions of this invention may also be used for treating Scabies. This is a disease found in man and animal. It is caused by *Sarcoptes scabie* and *Notoedres cati*. Scabies are caused by mites of Arachnida class *Sarcoptes Scabiei.*

The mite shows a preference for certain sites in which to burrow and appear to avoid areas with a high density of pilosebeceous follicle. The number of adult female mites in individual suffering from the common form of scabies is about twelve. Only in crusted scabies there are a large number of mites present.

Scabies is usually transmitted by close physical contact such as prolonged hand holding, bed sharing. Poor hygienic condition, encourage the spread of scabies. Scabies is usually found in developing countries and regions of poverty.

The pharmacological compositions of this invention when locally applied are scabicider and functions to minimize secretions from the sebaceous glands. Secretions from the sebaceous glands provide a suitable environment for the growth of mites in humans as well as in animals. The compositions provide a "double action" for the treatment of this disease.

The preferred treatment is with topical pharmacological compositions of a 2% to 10% (by weight) of a mixture of sodium citrate and citric acid or, alternatively with a 2% to 10% mixture of sodium oxalate and oxalic acid. Oral treatment for scabies may also be given for short period of time orally which also work as scabicider.

Fish Malodor

The pharmacological compositions of this invention may also be used for treating Fish malodor caused by sweating, vaginal discharge and/or from mouth and nares.

Trimethylaminuria (TMAU), also known as fish odor syndrome or fish malodor syndrome, is a rare metabolic disorder that causes a defect in the normal production of the enzyme flavin containing monooxygenase ("FMO3"). When FMO3 is not working correctly or if not enough enzyme is produced, the body loses the ability to properly convert trimethylamine (TMA) from precursor compounds in food digestion into trimethylamine oxide (TMAO) through a process called N-oxygenation. Trimethylamine then builds up and is released in the person's sweat, urine, and breath, giving off a strong fishy odor or strong body odor. Other names: Mal fish odor smell from sweating, Bromhidrosis and fish odor syndrome and osmidrosis.

Odor of skin in men to a large extend determined by apocrine glands secretion. Sebeceous glands secretions have some odor also. Decomposition of keratinization especially in the presence of hyperhidrosis produces offensive smell. Eccrine gland secretion is odorless but various substances may be excreted in it for example garlic.

Characteristic odors may be associated with various uncommon amino-acidurias; trimethyl-aminuria gives rise to the fish odor syndrome. This odor is unpleasant and people avoid sitting near such persons.

The pharmacological compositions of this invention act as a deodorant by rendering the application area anhidrotic. As it suppresses the sweat secretion of both apocrine and eccrine sweat gland it also suppressessebecous gland secretion sebum. It also prevents bacterial activity which decomposes and liberates fatty acids with its characteristic smell. The pharmacological compositions of this invention were used by 30 patients and the composition was efficacious.

The preferred treatment is with topical pharmacological compositions of a 2% to 10% (by weight) of a mixture of sodium citrate and citric acid or, alternatively with a 2% to 10% mixture of sodium oxalate and oxalic acid.

Vaginal Mal Fish Odor

The pharmacological compositions of this invention may also be used for treating vaginal mal fish odor. This is the commonest form of vaginitis. The patient complains of an excessive grey, thin discharge associated with a fishy odor. This disorder is associated with infection by aerobic Gram negative rod known as *Gardnerella vaginitis*. This organism alone is incapable of causing infection and now specific vaginitis is now regarded as complex interrelationship between *Gardnerella* and anaerobic species of bacteria of which genus *Mobiluncus* have been identified only and their over growth within the vagina give increase in secretion and fishy mal odor.

The preferred treatment is with topical pharmacological compositions of a 2% to 5% (by weight) of a mixture of sodium citrate and citric acid or, alternatively with a 2% to 10% mixture of sodium oxalate and oxalic acid.

Mal Fish Odor from Mouth

Mal fish odor from mouth and nose is a bad and unpleasant smell from the mouth and nose.

The preferred treatment is with a topical pharmacological composition of a 2% to 10% (by weight) of a mixture of sodium citrate and citric acid or, alternatively with a 2% to 10% mixture of sodium oxalate and oxalic acid.

Morphoea

The pharmacological compositions of this invention may also be used for treating Morphoea (Sclerosis of skin). Morphea is a medical term for localized scleroderma. The disease involves isolated patches of hardened skin—there generally is no internal organ involvement. The condition may be subdivided clinically into many types. In this disease skin become thickened, elastic tissue is reduced and the skin becomes hard. The surface is usually smooth and the wrinkles in the skin are lost. Facial expressions may also be lost.

The pharmacological compositions of this invention when topically applied cause resolution of such cases with excellent results.

The preferred treatment is with topical pharmacological compositions of a 2% to 10% (by weight) of a mixture of sodium citrate and citric acid or, alternatively with a 2% to 10% mixture of sodium oxalate and oxalic acid. From 1% to 2% salicylic acid and/or 0.025% to 0.05% clobetasol propionate may be added to the pharmacological composition.

Hypermelanosis

The pharmacological compositions of this invention may also be used for treating Hypermelanosis, a condition where there is excessive melanin deposition in the skin or in the oral mucous. This may be congenital or acquired through a drug reaction, melasma, addisions diseases, dyskeratosis congenital, post inflammatory hypermelanosis, berloque dermatitis, hypermelasnosis due to naevus of ITO, blue naevus, photodynamic and phototoxic reaction, hepatic cirrhosis (cause diffuse pigmentation), amyloidosis, pellagra, Mongolian spots and etc.

The pharmacological compositions of this invention when locally applied cures, diminishes or decreases such hypermelanotic pigmented spots.

The preferred treatment is with topical pharmacological compositions of a 2% to 10% (by weight) of a mixture of sodium citrate and citric acid or, alternatively with a 2% to 10% mixture of sodium oxalate and oxalic acid. Additionally, 0.025% to 0.05% clobetasol propionate and 2% to 3% salicylic acid may be added to the pharmacological composition.

Deformed Nails

The pharmacological compositions of this invention may also be used for treating Deformed Nails. Such nails are either congenitally or acquired through activity and environment. Without limiting the scope of the invention, there are several type nail deformities:
1. Habit deformity—the deformity consists of a depression down the center of one nail.
2. Splitting into layers—the tips of the nails split into layers and pieces may flake.
3. Onychogryphosis—the nail become curved like a ram's horn.
4. Beau's lines—a transverse depression in nails.
5. Regular pitting-Excess ridging with or without pitting.

The preferred treatment is with topical pharmacological compositions of a 2% to 10% (by weight) of a mixture of sodium citrate and citric acid or, alternatively with a 2% to 10% mixture of sodium oxalate and oxalic acid.

Nail Growth

The pharmacological compositions of this invention may be used to enhance the growth of nails which are broken before attaining its normal length.

The preferred treatment is with topical pharmacological compositions of a 2% to 10% (by weight) of a mixture of sodium citrate and citric acid or, alternatively with a 2% to 10% mixture of sodium oxalate and oxalic acid.

Hair Fall and Alopecia

The pharmacological compositions of this invention may also be used for effectively treating Hair Fall and Alopecia.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1.5% salicylic acid, 3% benzoic acid and 0.025% clobetasol propionate may be added.

Rosacea.

The pharmacological compositions of this invention may also be used for treating Rosacea. Rosecea is a chronic skin disorder, usually affecting the convexities of the face and characterized by redness of the skin, telengiectasia and episodes of inflammation. During an attack of inflammation the effected skin typically develops papules, pustules and swelling. The disease is common at ages 30-50 years old. The disease is also prominent in women.

Cardinal physical signs include 1) Erythema 2) Talengiectasia 3) Papules 4) Swelling 5) Pustules. The pharmacological compositions of this invention when therapeutically and locally applied reduce inflammation, anti-erythematic and keratolytic activity and reduce the number of episodes.

The preferred treatment is with topical pharmacological compositions of a 1% to 5% (by weight) of a mixture of sodium citrate and citric acid or, alternatively with a 1% to 5% mixture of sodium oxalate and oxalic acid. Additionally, optionally 5% to 10% zinc oxide may be added as sun screening agent and also as to prevent irritation to the composition.

Acne

The pharmacological compositions of this invention may also be used for treating acne. All types of acne may be treated.

Acne is chronic inflammatory disease affecting more than 80% of adolescents and may continue through adulthood. Some individuals suffer from acne into the thirties and even beyond. Lesion acne is most frequently found on face, neck and back, chest, shoulders and upper arms. Acne is characterized by the formation of comedones, papules, pustules, less frequently nodules or cyst and in some cases scarring. A peak of incidents is usually between 14 to 19 years. Four major factors in its pathogenesis Increased Sebum Production
1) Keratinization of pilosebeceous duct
2) Abnormality of microbial flora
3) Production of inflammation
4) Hydration The pharmacological composition of this invention when therapeutically locally applied inhibits sebum secretion and also inhibits sweat gland secretion and provides an anhidrotic skin area. The pharmacological compositions of this invention also have mild karatolytic activity and diminish keratinization. The antibiotic properties provide a sterile surface preventing or minimizing causative bacteria p-acne, as well as microbial flora. The composition also acts as an anti-inflammatory.

The preferred treatment is with a topical pharmacological composition of a 1% to 5% (by weight) of a mixture of sodium citrate and citric acid or, alternatively with a 1% to 5% mixture of sodium oxalate and oxalic acid. Optionally, 1% to 2% salicylic acid may be added. In severe conditions 0.5% to 1% hydrocortisone may be added for a short period of time. A widely used treatment for cystic acne is direct local injection into the cyst, which is very painful and may cause leocoderma on the skin, i.e., the skin becomes depigmented. With the treatment described herein, the cystic acne is treated with 2% to 5% of the pharmacological composition along with 0.025% to 0.05% Clobetasol propionate in suitable oil free cream applied locally. Such a treatment provides excellent results to dissolve cyst.

*Pityriasis rosea*

The pharmacological compositions of this invention may also be used for treating *Pityriasis rosea*. *Pityriasis rosea* is an acute and self-limiting disease. The exact cause of the skin condition is unknown, probably infective in origin, affecting mainly children and young adults and characterized by distinctive skin eruption and minimal constitutional symptoms. *Pityriasis rosea* eruption has been associated with drugs such as arsenic, bismith, gold, captopril, ketotifen, etc. The eruption of *Pityriasis rosea* follows a distinctive and remarkably constant pattern. Lesions are defined bright red, round or oval plaque, soon coved by fine scales. Lesions erupt in crops.

The pharmacological compositions of this invention when topically applied locally, the skin lesions subside within five to fifteen days. It is theorized that the mechanism of its action is keratolytic and anti-bacterial.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1% to 2% salicylic acid may be added.

Psoriasis

The pharmacological compositions of this invention may also be used for treating Psoriasis. Psoriasis is a genetically determined inflammatory and proliferative disease of skin, most characteristic lesions consisting of chronic, sharply demarcated, dull red scaly plaques. Provocative factors involved trauma, infection, sun light, metabolic factor drugs and etc.

The preferred treatment is with a topical pharmacological composition of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Lichen Planus

The pharmacological compositions of this invention may also be used for treating Lichen planus. Lichen planus is an immunologically mediated disease. Commonly presented as a skin lesion that is shiny, polygonal and violates papules. The lesion varies in size from a pin point to a centimeter or more and may be closely aggregated or widely dispersed. On the surface there may be Wickham's striae. Buccal mucosa and the tongue are most often involved but the anus and genitalia may also be involved. Lichenoid drug eruptions may occur due to certain drugs, for example, mepacrine, isoniazid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added. An oral composition may also be used for treatment.

Seborrhoeic Dermatitis

The pharmacological compositions of this invention may also be used for treating Seborrhoeic Dermatitis. It is a chronic dermatitis characterized by distinctive morphology including red sharply marginated lesions covered with greasy looking scales and a distinctive distribution in areas with a rich supply sebaceous glands namely the scalp, face and upper trunk. Dandruff appears to be the precursor of seborrhoeic dermatitis. The yeast *Malassezia furfur* is increased in seborrhoeic dermatitis. *P. ovale* is also found.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Tinea

The pharmacological compositions of this invention may also be used for treating *Tinea* (Fungal Infections). The present compositions are suitable as broad spectrum, topical antifungal preparations for the treatment oaf variety of fungal infections that may develop on the skin and nails, or which may be present and viable on surfaces which may come in contact with skin and nails. As a result, the compositions of the present invention may be used either therapeutically to treat a pre-existing infection, or as a fungicidal disinfectant to cleanse surfaces that may harbor the fungus, thereby preventing or limiting the occurrence of infections. The compositions are used to topically treat fungal infections that may develop on the skin (dermatomycoses) as well as toe and finger nails (onychomycosis). These fungal infections, also commonly known as *Tinea pedis* (athlete's foot), *Tinea unguium* (nail infections), *Tinea cruris, Tinea corporis, Tinea versicolor* and candidiasis, among others, are caused by different types of fungus such as those of the gena *Trichophyton, Epidermophyfon, Microsporum* and *Candida.*

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid, 5% to 10% zinc oxide may be added. An oral composition may also be used for treatment.

Oral Submucous Fibrosis

The pharmacological compositions of this invention may also be used for treating Oral Sub mucous Fibrosis. This disease can follow burns, irradiation but commonly and particularly this disease occurs due to habit of chewing of betel-nut which predisposed to oral sub mucus fibrosis. In such condition there is loss of elasticity of oral tissues. This disease is particularly found in Indian sub-continent. Pathologically there is fibrosis extending to sub mucosa and muscles. Epithelial changes included atrophy to keratosis. This disease, when severe, restricts the mouth from opening. The patient is unable to eat and even talk properly. This disease may transform into squamous cell carcinoma. Management of this disease is very difficult. Only intralesional corticosteroids injection locally has been found to help, otherwise surgery is needed. The pharmacological compositions of this invention when applied locally in a cream or in a jelly form have excellent (almost 100%) beneficial effect, resulting in the patient being able to reopen his/her of mouth to a large extent. Twenty-five (25) patients who were habitual chewers of the *betel* nut were the patients.

The preferred treatment is with a topical pharmacological compositions of a 2% to 10% (by weight) of a mixture of sodium citrate and citric acid or, alternatively with a 2% to 10% mixture of sodium oxalate and oxalic acid.

Amyloidosis

The pharmacological compositions of this invention may also be used for treating Amyloidosis. Amyloidosis is a disease in which there is a deposition of a proteinous substances composed of one of family of biochemically unrelated proteins which is associated with considerable dysfunction. Amyloid deposits also contain extra cellular matrix component including glycosaminoglycans and proteoglycans which may be involved in pathogenesis.

The pharmacological compositions of this invention were tested on papular (lichen) amyloidosis and upon macular amyloidosis in 24 patients and found to be effective.

Amyloidosis is classified as follows:
1) Primarily localized cutaneous Amyloidosis
2) Secondarily localized cutaneous Amyloidosis
3) Systemic Amyloidosis The pharmacological compositions of this invention are used to therapeutically treat skin (cutaneous) amyloidosis whatever the cause. My invention only treats and treated with success all skin conditions, where there is deposition of amyloid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Purpura

The pharmacological compositions of this invention may also be used for treating Purpura. Purpura is discoloration of skin or mucous membranes due to extra extravasations of red blood cells due to many causes. The skin becomes purpuric. Purpura may be caused by raised intravascular pressure. There are several types, e.g., senile purpura, corticosteroid purpura, drug purpura, contact purpura, schamberg purpura, coagulation defects purpura and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally, 0.025% to 0.05 clobetasol propionate may be added to the pharmacological composition.

Discoid Lupus Erythematosus.

The pharmacological compositions of this invention may also be used for treating Discoid lupus erythematosus. This disease is an autoimmune disease characterized by eruption of scaly patches atrophy, scarring and pigmentary changes, and most frequently involving the face. The disease affects twice as many females as males.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Contact Dermatitis

The pharmacological compositions of this invention may also be used for treating Contact dermatitis. Any antigen that comes in contact with skin may react with the skin causing contact dermatitis. It may be either primary irritant contact dermatitis or primary allergic contact dermatitis. For example, there is shoe dermatitis, hair dye contact dermatitis, nickel dermatitis, washing powder dermatitis, etc. The skin becomes scaly, pigmented and itchy and in some cases oozing.

The preferred treatment is with topical pharmacological compositions of a 1% to 10% (by weight) of a mixture of sodium citrate and citric acid or, alternatively with a 1% to 10% mixture of sodium oxalate and oxalic acid. Optionally 2% to 4% salicylic acid and/or 0.025% to 0.05% clobetasol propionate and 5% to 10% zinc oxide may be added as for sun screening agent and also for as soothing effect.

Hair and Skin Shiner

The pharmacological compositions of this invention may also be used as a hair and skin shiner. The compositions make the hair and skin shine, reflect the light causing an attractive look. This invention may be incorporated in shampoo and in face cream.

The preferred treatment is with topical pharmacological compositions of a 2% to 10% (by weight) of a mixture of sodium citrate and citric acid or, alternatively with a 2% to 10% mixture of sodium oxalate and oxalic acid.

Mollascum Contagious.

The pharmacological compositions of this invention may also be used for treating Mollascum contagious. This is viral infection of skin caused by an unclassified member of poxviridae in mollascum contagiousam lesion, characterized by papules and nodules. Its general treatment included cryotherapy, squeezing its forceps (a painful procedure), application of silver nitrate or phenol with stick and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid may be added.

Herpes Simplex

The pharmacological compositions of this invention may also be used for treating Herpes simplex. This is viral infection is caused by herpes virus hominis (herpes simplex virus, HSV). It is a common infection in men. Skin shows vesicles presenting as white plaques are present. Skin, tongue, buccal mucous membrane, palate, genital area and etc. are involved.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid and 5% to 10% zinc oxide may be added.

Paronychia

The pharmacological compositions of this invention may also be used for treating Paronychia. Paronychia is a painful full swelling of nail folds. It commonly occurs in persons whose hands are excessively exposed to water. It may result from local injuries for example nail biting, splits or there may be no preceding injuries. It is a common complaint and is usually due to bacterial infection including staphylococcal, other organisms involved in it may be *Streptococci, Pseudomonas, Proteus vulgars* and it may also be due to other causes for example fungal infection, *Candida albicans* infection, etc.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 2% to 4% salicylic acid may be added.

EXAMPLES

Preparation Active Composition

An equal amount of pharmaceutical grade sodium bicarbonate and citric acid by weight was placed in a sterile plastic container in an open room with a temperature at about 25 degree Celsius. The composition was mixed until a uniform mass was formed. A sufficient amount of purified sterile water was poured slowly into the mass to allow the reaction of sodium bicarbonate and citric acid. The mixture was left standing for 24 hours to allow the water and carbon dioxide to evaporate and for the product to dry. The mixture was again stirred to allow carbon dioxide and water vapors to further escape. A white crystalline and odorless powder was obtained. The final product contained 87% sodium Citrate and 13% citric acid as active ingredients. The measured pH of final product was 6. This solid composition was crushed and ground to a fine powder to produce an active composition that was pharmaceutically and physiologically acceptable, hereinafter the "pharmacological composition".

Sodium Citrate—Citric Acid Mixture

Stoichiometric Formulation Ratio:

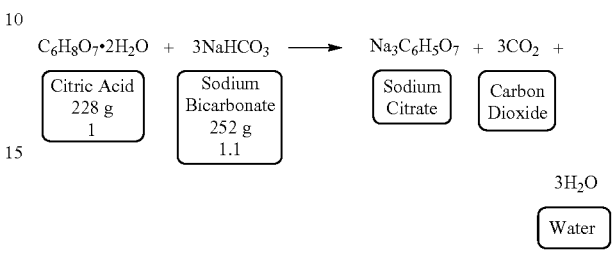

$$C_6H_8O_7 \cdot 2H_2O + 3NaHCO_3 \longrightarrow Na_3C_6H_5O_7 + 3CO_2 + 3H_2O$$

Method of Producing Active Composition:

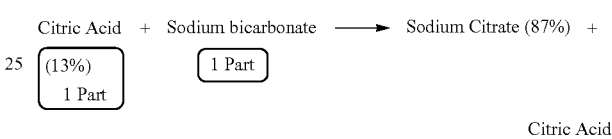

Citric Acid + Sodium bicarbonate ⟶ Sodium Citrate (87%) + Citric Acid
(13%) 1 Part
1 Part Chemical Equation with Structural Formulas:

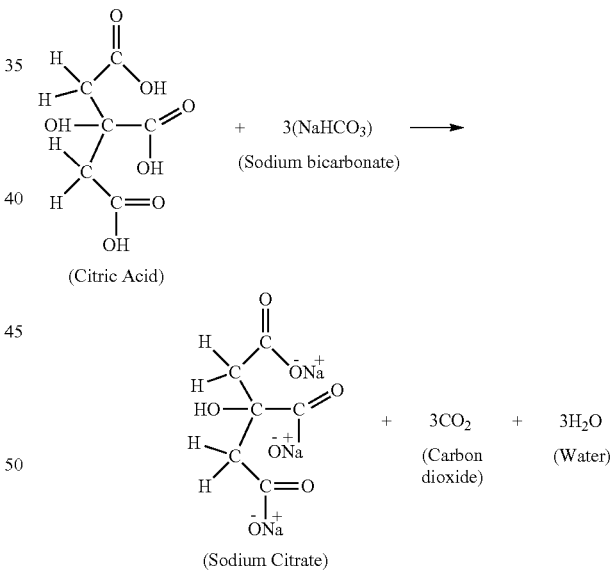

Structural Formulae of Active Ingredients:

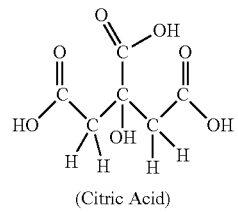

(Citric Acid)

-continued

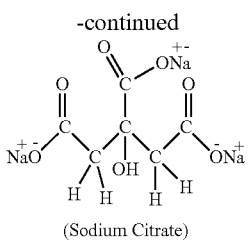

(Sodium Citrate)

In Vitro Study

Summary

The goal was to determine the susceptibility and activity of the powdered pharmacological composition produced on different bacterial strains at different concentration. The composition was a mixture of sodium citrate (stoichiometric ratio) and citric acid with the percentage of sodium citrate 87% and citric acid 13%, The procedure was to apply the powdered pharmacological composition of sodium citrate and citric acid to infectious bacterial strains and to determine susceptibility and activity of the pharmacological composition as anti-bacterial agent.

1. Material & Method:

Different infectious bacterial strains from different infected sites were selected, including pathogenic gram positive and gram negative bacterial strains. The activity of the powdered pharmacological composition on different bacterial strains was determined by applying it at different concentrations on various strains. In this study significant antimicrobial was observed when we used 300 mg and 500 mg of the pharmacological composition in dry powdered form.

The powdered pharmacological composition, i.e., a mixture of sodium citrate and citric acid with the percentage of sodium citrate 87% and citric acid 13%, was applied to infectious bacterial strains, including Gram Positive Organism (*Staphylococcus aureus Streptococcus* species and *Streptococcus* Gp D) and gram negative bacteria (*E. toll, Klebsiella* species, *Moragnella* species, *Enterobacter* species, *Serratia* species, *Salmonella typhi, Proteus* species) to determine susceptibility to anti-microbial activity of the composition.

A wire loop method was used to inoculate the bacteria on media plates. MacConkey Agar (Merck, Germany) was used for culturing of gram negative organism and blood Agar Media (Oxoid, England) was used for culturing the gram Positive Organism. For Confirmation and Identification of the organism, biochemical tests were done. For gram Negative Organism we used Triple Sugar Iron Media (Oxoid, England), Citrate Agar (Merck, Germany) Sulphide Indole motility media (Merck, Germany) Urea Agar (Oxoid,England) and for Gram Positive Organism we used Catalase test, Novabisin disk and manitol Salt Agar for Identification of *Staphylococcus aureus* and we also performed tube Coagulase test and for *Streptococcus* we did gram staining and Catalase test (showed negative Result).

2. Anti-Microbial Susceptibility Testing

A. The Gram Positive Organism Tested:
*Staphylococcus aureus*.
*Streptococcus* species.
*Streptococcus* gp D.

B. The Gram Negative Organism Tested:

1. Lactose Fermenting Bacteria:
E. coll.
*Klebsiella* species
*Enterobacter* species 2. Non-Lactose Fermenting Bacteria:
*Pseudomonas aeruginosa.*
*Proteus* species
*Morganella* species.
*Serratia* species.
*Salmonella* species.

In the present study anti-microbial susceptibility testing was done on Mueller Hinton Agar (Oxoid, England) using disk diffusion (Kirby Bauer's) technique. This method was done according to Clinical and Laboratory Standards Institute (CLSI) guideline to determine susceptibility of microbial agents.

Description:

The standard method used for determination of antimicrobial susceptibility is the disk diffusion procedure of Macfarland turbidity (Provided Powder used in replacement of disk)

Material Required:
Suitable agar & broth.
Provided Powder.
Sterile Cotton Swab.
Wire loop.
Medium: Mueller Hinton Agar (Oxoid, England)
Broth: Sterile peptone water (Oxoid, England)

Procedure:

Inoculum:
a) The inoculums were prepared by transferring a few identical colonies of different organism from the primary growth of Gram Negative (*Pseudomonas aeruginosa, E. coli Klebsiella* species, *Enterobacter* species, *Moragnella* species, *Proteus* species, *Serratia* species, *Salmonella* species) and Gram Positive (*Staphylococcus aureus, Streptococcus* gp D and *Streptococcus* species) with a wire loop in 2 ml of Peptone water (already filled in Sterile tube).
b) Incubate the Suspension at 35° C. for 10-15 minutes.
c) A sterile Swab applicator was dipped into the Culture Suspension. Excess suspension was removed by rotating it against side wall of tube, then streak on entire surface of medium in 3 different directions, by rotating the plate at 60° C. angle.

Placement of Pharmacological Composition (Antimicrobial Agent) (Powder) at Different Conditions and Concentrations:

After Streaking, the inoculum was allowed to dry for at least 5 minutes and inoculated with the powdered composition.

Pharmacological composition (antimicrobial agent) powder was applied: (50 mg)

For *Staphylococcus* (Resistant Strain and Sensitive strain:2 strains used), *Streptococcus* gpD *Streptococcus* species, *Pseudomonas aeruginosa, E. coli Klebsiella* species, *Serratia* species, *Morganella* species, and *Proteus* species)

Pharmacological composition (antimicrobial agent) powder was applied: (500 mg)

For *Klebsiella* species, *E. coli, Streptococcus species, Pseudomonas aeruginosa, Staphylococcus aureus Serratia* species, *Morganella* species, *Enterobacter* species and *Proteus* species.

Pharmacological composition (antimicrobial agent) powder was applied: (300 mg)

For *Klebsiella* Species, and different strains of *E. coli*.

The same procedure was used for 1000 mg

Incubation:

After the direct placement of the pharmacological composition (antimicrobial agent) was applied (50 mg) the concentrated disk on Mueller Hinton plates should be incubated aerobically at 35° C. for overnight.

Precautions:

For the proper interpretation of the results:

1. The suspension should always be made from pure culture and not from mixed culture.
2. The size of inoculum is uniform (avoid heavy/light inoculum).
3. The incubation condition must be of appropriate temperature and atmosphere.
4. The depth of the medium 4 mm (Approx. 25 ml medium in 100 mm plate)
5. The incubation period should not be less than 8 hrs. or more than 24 hrs.

Results:

In this study the organism showed different activities.

TABLE 1

Direct Antimicrobial Agent (Powder) applied at 50 mg Experiment.

| Bacteria | Used Quantity of antimicrobial agent | Result. |
|---|---|---|
| Gram Positive Bacteria: | | |
| *Staphylococcus aureus* | | |
| Strain 1 | 50 mg | Showed Activity |
| Strain 2 | 50 mg | Showed Activity |
| *Streptococcus* gp D | 50 mg | No-Activity Observed |
| *Streptococcus* species | 50 mg | No-Activity Observed |
| Gram Negative Bacteria: | | |
| *E. coli* | 50 mg | No-Activity Observed |
| *Klebsiella* species | 50 mg | No-Activity Observed |
| *Serratia*, species | 50 mg | No-Activity Observed |
| *Morganella* species | 50 mg | No-Activity Observed |
| *Proteus* species | 50 mg | No-Activity Observed |
| *Pseudomonas aeruginosa* | 50 mg | No-Activity Observed |

TABLE 2

Direct Antimicrobial Agent (Powder) applied at 500 mg.

| Bacteria | Used Quantity of antimicrobial agent | Result | Zone of inhibition Size |
|---|---|---|---|
| Gram Positive Bacteria: | | | |
| *Staphylococcus Aureus* | 500 mg | Showed Activity | 22 mm |
| *Streptococcus* species | 500 mg | Low effect showed | — |
| Gram Negative Bacteria: | | | |
| *E. coli* | 500 mg | Showed Activity | 25 mm |
| *Klebsiella* species | 500 mg | Showed Activity | 28 mm |
| *Pseudomonas aeruginosa* | 500 mg | Showed Activity | 43 mm |
| *Serratia* species | 500 mg | Showed Activity | 30 mm |
| *Morganella* species | 500 mg | Showed Activity | 30 mm |
| *Enterobacter* species | 500 mg | Showed Activity | 28 mm |
| *Proteus* species | 500 mg | Showed Activity | 25 mm |

*Zone size showed variation due to use of dry loose form of powder.

TABLE 3

Direct Antimicrobial Agent (Powder) applied at 300 mg.

| Bacteria | Quantity of antimicrobial agent | Result. | Zone of Inhibition Size |
|---|---|---|---|
| Gram Negative Bacteria: | | | |
| *E. coil* | 300 mg | Showed Activity | 45 mm |
| *Klebsiella* species | 300 mg | Showed Activity | 35 mm |

*Used different strains in of *E. coli* and *Klebsiella* species in Table 2 & 3

Discussion:

This study demonstrates the activity of the powdered anti-microbial agent, i.e., the pharmacological composition, against micro-organisms. This microbial agent (powder) or pharmacological composition also worked against those organisms which are normally highly resistant against other antimicrobial agents. Those organisms include *Pseudomonas aeruginosa, Staphylococcus aureus, Streptococcus* gp D.

In the first set of tests we applied the antimicrobial agent, i.e., pharmacological composition, in very low quantities (50 mg). Minimal activity was observed against Gram Positive (*Staphylococcus aureus Streptococcus* gp D *Streptococcus* species) and Gram Negative Strains (*Pseudomonas aeruginosa, E. coli Klebsiella* species, *Serratia* species, *Moragnella* species, *Proteus* species).

In the second set of tests condition we increased the quantity of antimicrobial agent (powder)—pharmacological composition—to 500 mg quantity of the powder which showed activity against bacteria Gram Positive bacteria (*Staphylococcus aureus Streptococcy* species) and Gram Negative bacteria (*Klebsiella* species, *E. coli Pseudomonas aeruginosa, Serratia* species, *Moragnella* species, *Proteus* species, *Enterobacter* species).

In the third set of tests we used different strains of *Klebsiella* species and *E. coli* and applied 3 00 mg antimicrobial agent (powder)—pharmacological composition—which showed activity against those bacterial strains.

Conclusions:

In this study minimal activity was observed after applying 50 mg of the anti-microbial agent. Significant zone sizes of inhibition were observed when the pharmacological composition was applied directly at 500 mg and 300 mg potency in powdered form.

It is believed that the mode of action of the pharmacological composition is to inhibit, topoisomerase enzyme which inhibits bacterial cell replication.

Clinical Trials

Oral Treatment of Bacterial Infection

I applied the pharmacological composition as anti-bacterial agent in numerous patients. The pharmacological composition contained 87% sodium Citrate and 13% citric acid as active ingredients. The measured pH of the final product was 6. This solid composition was crushed and ground to a fine powder to produce an active composition that was pharmaceutically and physiologically acceptable, hereinafter the "pharmacological composition" and then encapsulated, hereinafter the encapsulated pharmacological composition. Included herein are exemplary results from ten (10) patients.

Oral Application of Pharmacological Composition:

| Patient A | |
|---|---|
| Gender | Male |
| Age | 28 years |
| Diagnosis | Typhoid |

Present complaint: Patient complains of fever for the past week. Patient states that the fever fluctuates between highs and lows, and sometimes remains low but it does not reach normal. The patient is lethargic and feels week. Patient has also complained of abdominal pain for the past two days.

Examination: His fever is 99° F.; blood pressure is 120/70 mm of Hg. A Typhidot test for typhoid was positive, ESR 55 mm/hr., CBC (complete Blood Picture) report shows Hb 9.5 g/dl, TLC $14 \times 10^9$/L, Blood Culture report shows *Salmonella* typhoid. Typhoid fever is confirmed.

Treatment: The patient was given 500 mg of encapsulated pharmacological composition thrice daily and advice to take half an hour after food and revisit after 5 days.

Second Visit: Patient visited five days after initial visit to state that his fever subsided but not completely. The patient also said that his overall condition has improved. Patient was given same 500 mg encapsulated pharmacological composition and advised to continue to take thrice a day and revisit after five days.

Third Visit: Patient revisited five days after the previous date and indicated that his fever had completely subsided and that his weakness and other illness like condition had also subsided. The patient was told to repeat the same treatment of 500 mg of the encapsulated pharmacological composition thrice a day and advised to complete the therapy for further five days and then revisit for a blood culture and sensitivity report.

Fourth Visit: The patient was seen nine days after the Third Visit with complete satisfaction, as there is neither fever nor any other illness like condition. A blood culture and sensitivity report showed no bacterial growth. All treatment was stopped.

Patient B
Age 31 years
Gender: Female
Diagnosis: Tonsillitis

Present complaint: Patient complained that she was suffering from severe tonsillitis for 15 days. The patient complained of severe pain, itching, and irritation in throat. She developed hoarseness of voice. The patient said that she had chronic history of tonsillitis for the last 8 years. The condition remained off and on. When she developed a severity in her disease a consultant advised her broad spectrum antibiotic injection. After getting injections for at least 15 days, she obtained relief for 1 to 2 months.

Examination: Her throat was severely inflamed and there were enlarged tonsils with pustules with oozing purulent pus. The tonsils are grossly inflamed.

Treatment: The patient is given 500 mg of the encapsulated pharmacological composition twice a day and advised to return after 5 days.

Second Visit: Patient visited 5 days after her previous visit. Her tonsillitis and other inflammatory condition were reduced by about up to 50%. The patient was again advised to continue 500 mg encapsulated pharmacological composition twice a day and revisit after 5 days.

Third Visit: The patient visited 5 days after her previous visit. Her severe inflammatory condition and severe tonsillitis signs and symptoms were almost totally subsided; her hoarseness of voice and other complaints also subsided. To be on the safe side, the patient was again advised to continue 500 mg capsules twice daily for 5 days more since she had been suffering in this disease for the last 8 years. After taking this last dose she was told there was no need for additional visits unless she had complaints.

Fourth Visit: Patient visited 6 months after her last visit and was very happy and saying that after every 2 to 3 months she used to develop tonsillitis and used to get antibiotic injections. She has not developed tonsillitis her last treatment.

Patient: C
Age; 42 years
Gender; female
Diagnosis; UTI

Present complaint: Patient complains of burning micturition for the last 10 days.

Examination: Patient looked ill and appears to be tense and have 99° F. fever. A detailed report on urine shows pus cells 15-20/field and culture and sensitivity report shows growth of *E coli*.

Treatment: Patient was told to take 500 mg of encapsulated pharmacological composition twice a day and advised to revisit after 5 days.

Second Visit: Patient visited 5 days after the previous date and said that now she is feeling relief and now there is no burning micturition. Patient was advised to continue 500 mg encapsulated pharmacological composition for an additional 5 days and at the end of 5th day come with investigation report of urine detailed report on culture and sensitivity.

Third Visit: Patient visited 8 days after her last visit and said she was satisfied and that there no burning micturition, fever or other complaints. Her urine report showed no bacterial growth. Her treatment was stopped.

Patient: D
Age: 55 years
Gender: female
Diagnosis: Cholecystitis

Present Complaints: Patient complained of severe pain in right hypochondrium region for 8 days. Upon examination of investigations report, ESR 49. Ultrasound of upper abdomen shows cholecystitis and cholelithiasis Examination: Patient looked tense and anxious. Patient complained of nausea and vomiting. Upon examination of abdomen there was tenderness on the right hypochondrium.

Recommendations: Patient was advised to take 500 mg encapsulated pharmacological composition twice a day and revisit after 5 days.

Second Visit: Patient visited 5 days after previous visit and said there was relief in her pain and the nausea and vomiting had subsided. Patient was advised to continue the same remedy and dose for an additional 5 days.

Third Visit: Patient visited 5 days after the previous visit with complete relief in pain, nausea, vomiting and others sign and symptoms. Patient is again told to do the same treatment as previously, 500 mg encapsulated pharmacological composition for an additional 5 days to be on the safe side and advised to revisit after 5 days with an ultra sound report.

Fourth Visit: Patient visited 5 days after previous visit with ultra sound report which was normal, without cholecystitis. The treatment was stopped.

Patient: E
Age: 50 years
Gender: male

Diagnosis: Carbuncle

Complaint: Patient had a case of diabetes mellitus since 12 years and is on anti-Diabetic treatment. Twenty days prior to his visit he developed a nodule on the back of his neck which was gradually increasing in size and acquired big area and which started oozing and later on there was pus discharging from multiple orifices and severe pain.

Examination: There was a big lesion with multiple orifices with pus discharge and marked inflammation.

Investigation report: Shows high side Fasting and Random blood sugar.

Recommendations: Patient was given 500 mg 500 mg encapsulated pharmacological composition to take four times a day half an hour after food and advised to revisit after 5 days.

Second Visit: Patient's lesions were improved and there was a declination in inflammation, oozing and pus discharge. The patient had achieved some relief. The patient was advised to continue the same treatment of 500 mg encapsulated pharmacological composition four times a day and was advised to revisit after 5 days Third Visit: The patient visited 5 days after the previous visit and was greatly satisfied. There was a remarkable declination of the lesion area, remarkable declination in oozing and pus discharge and the inflammatory condition. The patient had achieved some relief. The patient was advised to continue the same treatment of 500 mg encapsulated pharmacological composition three times a day and was advised to revisit after 5 days.

Fourth Visit: Patient visited 5 days after the previous visit and was fully satisfied. Upon examination the lesion was completely cure. There was no inflammatory condition, oozing or pus discharge. There remained only a very peanut size dried nodule. To be on the safe side The patient was advised to continue the same treatment of 500 mg encapsulated pharmacological composition three times a day and for 5 days and advised that he need not return but to get proper treatment for the diabetic mellitus, as he was cured now.

Patient F
Gender: male
Age: 12 years

Diagnosis: Chalazion

Complaint: small, soft reddish nodule on right upper inner lid with slight pain and pus discharge for 10 days. He received treatment in the past, but there was no relief.

Examination: There was a markedly inflammatory soft peanut size nodule with slightly discharging purulent pus on right upper inner side of lid with conjunctivitis eye.

Recommendations: Patient was given 250 mg the crushed and ground pharmacological composition containing 87% sodium citrate and 13% citric acid in neutral syrup thrice a day half an hour after food and was advised to revisit after 5 days.

Second Visit: Patient visited 5 days after previous visit and his mother said that he has obtained substantial relief, the lesion was reduced and the redness in his eye also declined. Upon examination the nodule was reduced, pus discharge had ceased, and the conjunctivitis was in decline. The patient was advised to repeat the treatment for another 5 days, i.e., 250 mg the crushed and ground pharmacological composition containing 87% sodium citrate and 13% citric acid in a neutral syrup thrice a day half an hour after food and was advised to revisit after 5 days.

Third Visit: The patient visited 5 days after previous visit and was satisfied. There was no complaint of pain, redness, nodule, discharging pus, or conjunctivitis in eye. There appeared to be a remnant of a lesion. The patient was given same remedy with same dose for an additional 5 days to be on safe side, advised to stop treatment after that and that there was no need to visit again because you are cured.

Patient G
Gender Female
Age 36 years
Rx Paronychia

Complaint: Patient complains of pain, swelling and pus discharge from the nail fold of right index finger for about one week.

Examination: There was swelling and purulent pus discharge and an inflammatory condition. The case was diagnosed as Paronychia.

Recommendations: Patient was given 500 mg encapsulated pharmacological composition twice a day and advised to revisit after 5 days.

Second Visit: Patient visited 5 days after previous visit and had achieved more than 75% relief. Upon examination the swelling, discharging pus, inflammatory condition and pain had subsided to a large extent. Patient was given 500 mg encapsulated pharmacological composition twice a day and advised to revisit after 5 days.

Third Visit: Patient visited 5 days after the previous visit and was fully satisfied as there were neither complaints of pain. Upon examination there was no swelling, pus discharge or inflammatory lesions. The patient was completely cured and treatment was stopped Patient: H
Gender: Male
Age: 52 years Diagnosis: Acute exacerbation of chronic bronchitis.

Complaints: Patient complained of a history of chronic bronchitis for the last three years where he gets attacks of fever and severe attacks of cough with purulent sputum and preventing him from obtaining sleep for the past year. He has a history smoking for thirty years. Two months ago the symptoms were not present but as the weather changed he has again developed fever, cough with purulent sputum for the last week. He was told that he has an acute exacerbation of chronic bronchitis.

Examination: Patient had a fever, on auscultation there is wheezing and crepitation on chest.

Recommendations: Patient was given 500 mg encapsulated pharmacological composition four times a day half an hour after food and advised to revisit after five days.

Second Visit: Patient revisited five days after previous visit and says that he obtained some relief but still has a cough with purulent sputum. He was still running a fever but the temperature slightly subsided. Patient was again given 500 mg encapsulated pharmacological composition four times a day half an hour after food and advised to revisit after five days.

Third Visit: Patient visited five days after the previous visit and was highly satisfied in that he had obtained much greater relief and there was no fever. However, his cough and purulent sputum had only somewhat subsided, but now sleeps deeply and comfortably. Patient now complained of dizziness and was given anti-motion therapy. Patient was again given 500 mg encapsulated pharmacological composition three times a day half an hour after food and advised to revisit after five days.

Fourth Visit: The patient visited five days after previous visit with full satisfaction and says that now he was in relief and there was no fever, cough or sputum nor complaint of dizziness after taking anti-motion drug. To be on the safe side the patient is again given same 500 mg encapsulated pharmacological composition but now only twice a day for an additional five days and then stop treatment for he is now cured.

Patient: I
Gender: female
Age: 25 years
Diagnosis: cellulitis (skin and soft tissue infections)
Complaint: Patient is 24 weeks pregnant and complains redness and pain on upper front of left thigh and also complains of fever for past five days.

Examination: There was redness and an inflammatory condition on the front of left thigh. On touching the lesion, it was warm and tender and there was tenderness.

Recommendations: The patient was given 500 mg encapsulated pharmacological composition twice a day, half an hour after food and advised to revisit after five days.

Second Visit: Patient visited five days after previous visit with declination of lesion and inflammation tenderness. Her fever had subsided. The patient had complained of slight nausea and vomiting. The patient was given 500 mg encapsulated pharmacological composition twice a day, half an hour after food. She was also given nausea and vomiting anti-emetic drug. Patient was advised to revisit after five days.

Third Visit: Patient visited five days after previous visit with marked declination of signs and symptoms. There was no fever, tenderness, pain or inflammatory condition. There was still a complaint of nausea and vomiting and she was given anti-emetic. Patient for safety was advised to repeat the 500 mg encapsulated pharmacological composition twice a day, half an hour after food for an additional five days to reduce all signs and symptoms.

| Patient B | |
|---|---|
| Age | 31 years |
| Gender: | Female |
| Diagnosis: | Tonsillitis |

Diagnosis: Sub acute appendicitis

Complaints: Patient complained of an on and off pain in right hypochondrium for the last three days. The patient also complained of nausea with episodes of pain. The patient also complained of fever for the past three days. Patient also complained of the same symptoms twenty days back.

Examination: There was tenderness on the right hypochondrium and there was a low grade fever also.

Recommendations: The patient was given 500 mg encapsulated pharmacological composition twice a day, half an hour after food and advised to revisit after five days.

Second Visit: The patient revisited five days after previous visit. The signs and symptoms had subsided. Upon examination there was less tenderness and there was also no fever. The patient was given 500 mg encapsulated pharmacological composition twice a day, half an hour after food and advised to revisit after five days. The patient was also advised to consult a General Surgeon for his opinion because the appendix might burst, which might cause peritonitis and poisoning with a fatal outcome. The therapy recommended herein reduced all signs and symptoms and had arrested the growth of bacteria, reducing inflammation.

Third Visit: Patient revisited five days after previous visit with complete satisfaction. All signs and symptoms were reduced. The surgeon advised that if he again feels severe pain than he will operate to remove the appendix. If there are no complaints there is no need to operate. All therapy stopped.

Side Effects and Drug Interaction Observed

No serious side effects were observed in any patients. The only side-effects observed, were nausea and vomiting and some dizziness in about 0.5% of the patients. One in 500 patients developed a minor allergic reaction which subsided when treated with an anti-histamine drug. There were no drug interactions noted with anti-coagulant drugs. No serious adverse effects were observed in patients or any life-threatening conditions as Steven-Johnsons syndrome or anaphylactic shock with oral therapy.

EXAMPLES

Treatment of Deformed Nails

An embodiment of this invention relates to ameliorating, preventing and/or treating nail deformity, slow nail growth/retardation due to either systemic or local skin diseases. The pharmacological compositions of this invention may be used to enhance the growth of nails which are broken before attaining its normal length.

The preferred treatment is with topical pharmacological compositions of a 2% to 10% (by weight) of a mixture of sodium oxalate and oxalic acid. The method of treatment of such nail growth symptoms comprises topically applying to the nails a composition comprising a mixture of sodium oxalate and oxalic acid with specific ratio by percentage, by weight and a physiologically acceptable carrier vehicle. The highly preferred composition is a mixture of 78.44% sodium oxalate and 21.56% oxalic acid. A preferred range is about 73% to about 83% Sodium oxalate and about 17% to about 27% oxalic acid. It is to be understood however that various weights and ratios of sodium oxalate and oxalic acid may be used as long as a safe and efficacious pharmacological composition is produced. Optionally, the composition applied consists of a mixture of sodium oxalate and oxalic acid and an effective amount of hydrocortisone, e.g., about 1% by weight of hydrocortisone.

The method of this invention is effective, low cost, and easily applied. The composition used is easy to manufacture as demonstrated herein and is effective in the treatment of deformed nails, e.g., nail diseases, to ameliorate, prevent and/or treat such diseases.

The method for treating the deformed nails and nail diseases herein comprises topically administering or applying a composition, comprising a sodium oxalate and oxalic acid mixture with specific ratio by weight and percentage to the nails of a mammal, typically a human. More specifically, the method comprises applying a pharmacological composition to the patient's fingers or toe nails. The amount of the composition applied is a therapeutically effective amount of the composition that will ameliorate, prevent and treat nail diseases/deformed. The patient should avoid contacting his/her eyes with his/her fingers after treatment.

Pharmaceutical Carrier

Examples of the pharmaceutical carrier and the method of preparation that may be used are provided herein.

A. Oil and water base vehicle (base) preparation (100 grams on small scale):

Vessel A—Take 75 grams purified and sterile water in suitable container like stainless steel vessels and heat it to 70° C.

Vessel B—Take 25 gram of a pharmaceutical grade emulsifying wax and melt it by heating up to 70° C. in a water bath.

Mix the heated water into heated emulsifying wax stirring slowly until the mixture is uniform and the temperature of mixture decreases to about 35° C. then cool. The pharmaceutical carrier thus contains 25% emulsifying wax and 75% water by weight.

Pharmacological Composition

Composition A:

5% sodium oxalate and oxalic acid mixture incorporated in the pharmaceutical carrier, i.e., 25% % emulsifying wax and 75% water. Optionally, a preservative may be added.

Composition B: 5% sodium oxalate and oxalic acid mixture and 1% hydrocortisone incorporated in the pharmaceutical carrier, i.e., 25% % emulsifying wax and 75% water.

Treatment Procedures and Clinical Results

Patient: A

Age: 36
Gender: Male
Status: Married, low socio-economic
History or Complaints of Patient:

Patient complains that his nails were normal with natural shape two years back, then gradually the nails began to develop pin head size depressions on nails surface of two nails. With the passage of time, gradually these depressions increased in other fingers nails also and within the period of 3 years, most of the nails have pin head size depressions. Patient does not give any history of depression in toe nails On Examination of Patients:

On examination of the patient, no existing lesions or signs were found of any existing skin disease, although his skin appears to be dry. There was no history of any systemic disease or skin disease. On examination of the nails of the fingers pitting was observed on most of his nails but there were no depressions (pitting on toes nails) except that his all nails were rough and dry.

Diagnosis: Diffused pitting on the finger nails.

Treatment and Advice:

Patient was given Remedy A and advised to apply it locally on the affected nails twice a day and revisit after 20 days.

Patient $2^{nd}$ Visit:

Patient revisited 20 days after the first visit to say that his nail depressions were declining. On examination his pitting nails were filling. The patient was given the same Remedy A to apply in the same manner as previously and advised to revisit after 20 days.

Patient $3^{rd}$ Visit:

Patient visited one month after previous date. 75% of the nails pitting depressions were filled. Patient was again given same Remedy A with the advice to revisit after one month Patient $4^{th}$ Visit:

The patient visited one month after his previous visit and was quite happy because all the nail depressions were substantially filled and his nails were shining. On examination 90% of the pitting was filled. The patient was again given the same Remedy A and advised to revisit after one month.

Patient $5^{th}$ Visit:

Patient revisited one month after the previous visit. All nail depressions were almost completely filled. Examination revealed that approximately all depressions had disappeared and the nails had luster and were shining. The patient treatment was stopped and the patient was advised to keep his nails moisturized.

Patient: B
Age: 21
Gender: Female
Status: Unmarried, College student.
History or Complaints of Patient:

Patient complains of that her nails were fine 6 years ago when she developed a depression in the middle of the right thumb nail which gradually increased in size to form a canal like structure in the nail. Subsequently fine cracks extended from the canal like structure to the edges of the nail on each side.

On Examination of Patient:

On examination of all nails of the hands and feet only the right thumb nail shows a canal like depression and the cracks projecting towards and reaching the edges of the nail on each side. Her history did not reveal any skin or systemic diseases.

Diagnosis: median nail dystrophy of heller.

Treatment and Advice:

Patient was given Composition A and advised to apply locally twice a day and revisit after one month.

Patient $2^{nd}$ Visit:

Patient visited one month after the first visit and said that canal and cracks are filling. On examination of the affected nail, canal and cracks were filled up to 40%. Patient was advised to revisit after one month again.

Patient $3^{rd}$ Visit:

Patient revisited one month after the previous visit and was very happy to say that she is getting cured and the canal and cracks are being filled. On examination there was 70% of filling of depressed nail. The patient was given the same Composition A and advised to revisit after one month.

Patient 4th Visit:

Patient revisited one month after the previous visit. Her depressed nail canal was substantially filled. On examination, there was 90% filling of affected nail. She was given again the same Composition A to apply in same manner as previous and advised to revisit after one month.

Patient $5^{th}$ Visit:

On her fifth visit one month after the previous visit the nail canal and cracks were filled completely filled. Treatment was stopped and she was advised to return in one year.

Patient $6^{th}$ Visit:

Patient came one year after the last visit. She was 100% cured as it was at the time last attended. There were no developments of any canal or cracks.

Patient: C
Age: 12
Gender: Male
Status: Student of class 5, High socioeconomic
History or Complaints of Patient:

Mother of patient states that her son nails of fingers and toes do not grow normally and does not increase in size as others grow. She complains that these nails are not broken but have slow and limited growth. She said that after 2 to 3 months, it grows slightly but growth is restricted.

On Examination of Patients:

On examination of patient, nails of child of hands and toes are below normal growth. On examination of patient, there is no lesion in skin which could indicate any sign of skin disease. Mother does not give any history of systemic disease except that patient appears to be anemic.

Diagnosis: Slow rate of growth of nails of hands and Toes

Treatment and Advice:

Patient is given Composition B to apply locally twice a day and revisit after 15 days Patient $2^{nd}$ Visit:

Patient revisited 15 days after the first visit. Mother says that there has been an improvement in growth. Patient is given the same Composition B to apply twice a day in the same manner and revisit after one month.

Patient $3^{rd}$ Visit:

Patient revisited one month after the previous visit. Mother says that his nails of toes and fingers are growing and the size of nails has been increased. Patient is given the same Pharmacological Composition B to apply twice a day and revisit after one month.

Patient 4th Visit:

Patient revisited one month after the previous visit. His nails of hands and feet have become excellently increased in size. Mother says that now she is cutting his nails. Patient is given now Composition A to apply twice a day and revisit after one month.

Patient $5^{th}$ Visit:

Patient visited one month after the previous date and now the nails have become normally growing and increasing in size as per mother says. On examination of nails, nails had become normally grown. Patient is given again Composition A to apply locally twice a day and afterwards stop the medicine. Mother is also directed to revisit anytime if she feels that after the stoppage of medicine if growth is slow.

Patient $6^{th}$ Visit:

Patient visited 6 months after the previous date to say that his nails are growing normally.

Patient: D

Age: 17

Gender: Female

Status: student of first year college

History of Complaint of Patient:

Patient states that her nails were in normal texture three years back while started to develop pin head depression of hand nails fingers. With the passage of time, these depressions developed in other nails also. Patient also gives the history of loss of hair on scalp at three spots.

On Examination of Patients:

On examination of nails of patients, there were pin head depressions in fingers nails. On examination of her skin, there was loss of hair at three spots. Patient did not have any history of a systemic disease.

Diagnosis:

Pitting on nails of hands due to the disease Alopecia areata

Treatment and Advice:

Patient is given Composition B to apply locally on affected nails twice a day and advised to re-visit after 20 days.

Patient $2^{nd}$ Visit:

Patient visited 20 days after the first visit and says that her depressions of nail are appearing to be filled. On examination, of her nails depressions were reduced slightly. She is advised to revisit after one month. She is given same Composition B to be applied locally twice a day in same manner as previously.

Patient $3^{rd}$ Visit:

Patient revisited one month after the previous date with marked improvement. On examination of her nail, depressions were filling. Patient was given same Composition B and advised to revisit after one month and apply the medicine in same manner as previously.

Patient 4th Visit:

Patient visited one month after the last visit with excellent marked improvement. Patient is given Composition A to apply in same manner locally twice a day and revisit after 15 days.

Patient $5^{th}$ Visit:

Patient revisited one month after the last visit with complete cure and there were no pitting depressions in any of the nails. The treatment is now stopped and advised to revisit if he feels any depression.

Patient $6^{th}$ Visit:

Patient visited 7 months after the last visit to complain that she is again developing depression in two nails. She is again given the Composition B to apply only at night in all fingers nails and visit after 6 months.

Patient: E

Age: 12

Gender: Female

Status: Student, Low socio-economic

History or Complaints of Patient:

Mother of child complains that nails of fingers and toes of her daughter are flat rather than convex and are adherent to nail beds since her childhood and even there is no shining in her nails.

On Examination of Patients:

On examination of patient, her fingers and toe nails are flat and lusterless. By examining her whole body skin, there found no any sign of skin disease. Patient mother does not give any history of current or previously of systemic disease except that she does not eat properly. She also complains of loss of appetite only. She also told that all her blood reports are normal which were done one month back. On examination, all nails of fingers and toes are flat and appear to adherent to nail beds.

Diagnosis: Flat nails of fingers and toes

Treatment and Advice:

Patient is given Composition B to apply locally twice a day and advised to keep nails moisturized. Patient is directed to revisit after 20 days.

Patient $2^{nd}$ Visit:

Patient Revisited 20 days after the first visit. Her mother states that her nails are somewhat raised to nail beds. On examination of patient nails of hand and feet, appears to slightly rise. Patient is advised to revisit after one month.

Patient $3^{rd}$ Visit:

Patient revisited one month after the previous date. Mother says that nails are improving and rising from the nail bed. On examination nails are raised. Patient is given now again Composition B and advised to revisit after one month.

Patient 4th Visit:

Patient visited one month after the previous date. Her mother seem to be very happy and states that all of her nails with the exception of two nails has become completely normal with raised to nail bed and have acquired convexity and luster also. Now patient is given Composition A for maintenance and advised to apply furthermore and revisit after one month.

Patient $5^{th}$ Visit:

Patient visited one month after the previous visit and says that her all nails have become normal now with convexity.

On examination of patient nails, nail had become normal. Drug is stopped and advised to patient keep her nails moisturized Patient 6$^{th}$ Visit:

Patient visited one year after the previous date with complete cure and no reoccurrence of diseased.

Patient: F
Age: 40
Gender: Male
Status: Married, high socioeconomic, Engineer
History of Complaints of Patient:

Patient complains of deformed, roughness with strie nail for the last one year. He says that his all nails were normal one year back while he felt to develop roughness and strie in his index fingers of left nail in spite of getting different treatment, it was not going to be improved. He also says his rest of nails are normal.

On Examination of Patients:

On examination of patient, all of his nails of fingers and toes are of normal texture except roughness deformed and strie in left index fingers. Patient does not give history of any skin disease. I examined whole of his skin, he has no skin lesions at any spot. Patient gives the history of Diabetes Mellitus for the last 3 years. Except Diabetes Mellitus, he has no other systemic disease Diagnosis: Deformed Rough strie nail.

Treatment and Advice:

Patients is given Composition A and advised to apply locally twice a day and visit after one month.

Patient 2$^{nd}$ Visit:

Patient visited one month after the previous visit and said that he has got improvement; the nail growing from proximal is being corrected. He also says that nail growth is also increased. He is cutting nail and the nail from growing place emerging normal. On examination, there is marked improvement. Patient is given same Composition A and to apply in same way and advised to revisit after one month.

Patient 3$^{rd}$ Visit:

Patient visited one month after the previous visit with remarkable improvement ad was very happy to say now his deformed nail of index fingers has adapted normal texture. On examination his nail is growing from proximal is adapting normal texture declining of lining and deformity. Composition A is given to apply locally and advised to revisit after one month.

Patient 4th Visit:

Patient revisited one month after the previous visit with highly remarkably improvement. Nails proximally growing are attending normal texture and declining lining stria and deformity. Patient is given same Composition A and is advised to revisit after one month.

Patient: G
Age: 18
Gender: Female
Status: Unmarried, Student and Low Socio Economic.
History of Complaints of Patient:

Patient states that her nails were with normal growth and structure while she felt splitting of her fingers nails in her two fingers, while the small pieces may flake and the nails grow and flake at the tip of the fingers which gradually developed to split and flake in whole nails fingers of hands.

On Examination of Patients:

On examination of the patient her whole fingers nails of hands were split into pieces and the growth of nails were restricted till tip of the fingers. On examination of the nails, nails are lusterless also further examination of her skin there is no any indication of skin disease. She says that her hands remain mostly in water. She is not giving any history of current or previous systemic or any skin diseases.

Diagnosis:

Splitting of nails into layers (onychoschizia) (Lamiler Dystrophy)

Treatment and Advice:

Patient is given Composition B and advised to apply locally twice a day and revisit after 20 days. Patient is also advised to remain away from water and also keeps her nails moisturized.

Patient 2$^{nd}$ Visit:

Patient visited 20 days after previous visit and says that her nails are improving and now the splitting of nails is declined up to an extent. Patient is given same Pharmacological Composition B and advised to apply in same way as previously and revisit after one month.

Patient 3$^{rd}$ Visit:

Patient visited one month after previous visit and is very happy as she says that her splitting of nails has been subsided to a great extent and her nails are growing without splitting now beyond the tips of fingers. Now she is given Remedy A and advised to apply the medicine locally as previously and revisit after one month.

Patient 4th Visit:

Patient visited one month after the previous visit and says that now her nails are 90% improved and very less splitting than before. On Examination of her nails there appears to be not any deformity. Patient is given the remedy A for maintenance and advised to revisit after one month.

Patient 5$^{th}$ Visit:

Patient visited one month after the previous visit and says that now she has got 100% cure and there is no splitting of nails. On examination her nails appears to be normal the treatment is stopped and advised the patient if she feels any problem she can come back or normally revisit after 6 month.

Patient: H
Age: 52
Gender: Male
Status: Married, Labor, Poor Socio Economic
History or Complaints of Patient:

Patient complains of his brittle nails since last 6 months in his all nails of hands and feet fingers. He also complains of lusterless and dry nails. Patient says that his nails are brittle and breaking since 6 months.

On Examination of Patients:

On examination of patient, his nails are brittle and lusterless. His all fingers and toes nails are affected. On examination of his skin there is no any lesion on skin. Even patient doesn't give any current or previous history of skin or any systemic diseases except that 8 months back he had iron deficiency anemia for which he had got treatment and his anemic condition was improved. Patient says that after correction of his even anemic condition, he felt brittleness in his nails. Although his anemic condition is corrected but nails are still brittle.

Diagnosis:

Brittle of nails due to iron deficiency anemia.

Treatment and Advice:

Patient is given Composition A and advised to apply locally twice a day on affected nails. He is also advised to take diet properly and revisit after one month.

Patient 2$^{nd}$ Visit:

Patient visited one month after previous visit and says that now his brittle nails are improving. His nails are growing rapidly and nails from proximal end are correcting. He is given same Composition A and advised to revisit after one month.

Patient 3$^{rd}$ Visit:

Patient visited one month after the previous visit and says that his nails are improved more. He is given same Composition A to apply locally twice a day and advised to revisit after one month.

Patient 4th Visit:

Patient visited one month after the previous date and says that he is now improved up to an extent. Nails from proximal ends are adopting normally and are not brittle. Same Composition A is given and advised to revisit after one month.

Patient 5$^{th}$ Visit:

Patient visited one month after the previous date and says that there is marked improvement. Nails are returning back to its previous condition but still somewhat brittle. Same Composition A is given and advised to revisit after one month.

Patient 6$^{th}$ Visit:

Patient revisited one month after the previous visit with near about complete cure. His remedy is stop and advised to keep his diet balance also.

Patient: I
Age: 8 yrs.
Gender: Male
Status: Primary class student
History or Complaints of Patient:

Patient's mother complains of her child that his nails do not grow beyond the tip of fingers for the last one year. Mother states that his nails of both hand's fingers were normal two years back. But after that all fingers nails of both hands are not growing beyond the tip of fingers. Mother also says that his toes fingers nails are growing normally On Examination of Patients:

On examination of all nails of toes and fingers, toes nails are normal but fingers nails of both hands growth are restricted at the tip of the fingers. On examination of hands fingers nails appears to be bitten and after asking the mother, She told that he was habitual of biting his fingers nails after that nails restricted to grow but even after leaving the biting of nails since last six months, even though nails are not growing normally. These restricted growths of nails are due to continuous biting of nails.

Diagnosis: Diminished nail growth due to biting.

Treatment and Advice:

Patient is given Pharmacological Composition B to apply locally on all fingers nails twice a day and advised to keep the nails moisturized. Patient is advised to revisit after one month.

Patient 2$^{nd}$ Visit:

Patient revisited one month after the previous visit. Mother states that his nails are now growing. Same Composition B is given to apply in same way as previously and revisit after one month.

Patient 3$^{rd}$ Visit:

Patient revisited one month after previous visit. Mother is very happy to say that nails have started to grow normally. On examination of nails of patients, nails are grown beyond the tip of the fingers. Patient is given now Composition A to apply in same manner as previously and advised to revisit after one month.

Patient 4th Visit:

Patient visited one month after the previous visit. Mother is now very happy to say that now she is cutting the nails of his child and afterwards these nails are growing. Medicine is stopped and patient is advised to moisturize his nails. Patient is also advised not to apply any medicine and revisit just for checking after 6 months.

Patient 5$^{th}$ Visit:

Patient visited 6 months after the previous date for checkup. Mother is very happy to say that now his nails are growing properly and normally as these were before the disease.

Patient: J
Age: 72
Gender: Male
Status: Labor, Lowest socioeconomic, neglected
History or Complaints of Patient:

Patient complains of his deformed nail of right foot big toe nail. He complains that he has come to you because of the deformed nail with raised from the nail bed and has acquired a strange shape. Patient also complains of severe pain if it is touched to any solid object. He also says that he does not remember the time period but it is since long time.

On Examination of Patients:

On examination of the toe's nails of the patient, it resembles like RAM'S HORNS. Patient looks and attitude is appearing to be deficient in diet and is neglected person in the society. He is Labor and he says that no one does care of him in his family. He even does not cut his nails since long time. He also says that he had to face trauma in his nail so many times. His wife was died 8 years back and now days no one keeps care of him. On overall examination, his all nails are not in normal texture, some nails have got style and some are brittle but he came to me because his one toe nail is creating great problem for him as he gets severe pain in it whenever it is touched to anything. He does not give the history of any local or systemic diseases but by appearance appears to be deficient in diet. Patient gives the previous history of surgical removal of this nail but it reoccurred like same Diagnosis: Onychogryphosis (Ram's Horn Nails)

Treatment and Advice:

As there is no specific treatment of it but Some recommend avulsion of the nail plate with surgical destruction of the nail matrix with phenol or the carbon dioxide laser, if the blood supply is good. Even after getting treatment of surgical destruction, Patient again develop same Ram's Horn like nails within 3 months. I first adopted the Treatment to cut the ¾$^{th}$ nail which was raised from the nail bed and laid the rest of the nail remaining as it is. Then I gave the patient Composition B to apply locally from the remaining part of nail so that nail from the root might be growing normally and remain attached to nail beds. Patient is advised to keep the nails moisturized and revisit after one month.

Patient 2$^{nd}$ Visit:

Patient visited one month after the previous date to say that his growing nails are appearing to be coming with the attachment of nail bed. On examination of his disease nail, Nail appear to be somewhat growing normally proximally and still are raised from the bed but very little. Patient is given the same Composition B and advised to apply the drug in same way locally twice a day and revisit after one month.

Patient 3$^{rd}$ Visit:

Patient visited one month after previous visit to say it is improving. On examination, Nail growth was increased and the nail was attached to nail bed somewhat but not like previously raised. Patient is again given the same Composition B and advised to revisit after 2 months and keep the nails moisturized.

Patient 4th Visit:

Patient visited 2 months after the previous date to say that now the nail have been improved to an extent and it is not raised from the nail bed too much. He is also not feeling pain. Patient is given again the same Composition B and advised to revisit after 3 months again.

Patient 5$^{th}$ Visit:

Patient visited 3 months after the previous visit with the complete eruption of new growth of nail and is very happy but says that still it is raised from the nail bed but not like previous one like Ram's horns and is improved and not feels pain even if it is touched with any of the object. Patient is given the same Composition Band advised to revisit after 3 month and advise to apply the drug locally in same way as previously.

Patient 6th Visit:

Patient visited 3 months after the previous visit with quite happy and says that now his most of the proximal part of the nail have become normal and is attached to nail bed but distal part still raised from the nail bed but he does not feel any pain. On examination of hi affected nail, it has adopted normal texture up to a great extent and the half of the nail are attached with the nail bed and the distal part of nail is still raised from the nail bed but not to that extent as it was previously. Nail from the proximal part is getting normal texture. Patient is cutting his nail as it grows beyond the tip of the finger. Patient is given now Composition A to apply locally as previously and maintenance dose and advised to apply it regularly for two to four months more and revisit afterwards.

Patient 7th Visit:

After the last visit, Patient did not come back.

The active compositions of this invention are rapidly and highly soluble in water and thus are rapidly absorbed onto and into nails, wet skin rather than on dry skin. It is thus preferred that the compositions be topically applied to skin/nail surface that has been moistened with water.

As the active composition when applied to the skin can create dryness, it is thus desirable to have a formulated pharmacological composition that is greasy. However, when treating acne this drying ability is beneficial and thus the final composition should be non-greasy or have less of a greasy feel or property.

The active compositions are rapidly absorbed per cutaneously and enter in to the bloodstream. Therefore it is advisable that when the drug is applied to a large area, for example in the treatment of psoriasis, the patient should be kept under observation by the physician.

The active composition may also lower blood pressure as it is absorbed through the skin. It is thus advisable not to treat patients less than 5 years old or applied under strict supervision at a low concentration of active composition and/or treating small areas.

If given orally it may cause nausea, vomiting and diarrhea. It therefore should be taken a half hour before food or one hour after food.

Treatment of Hair Loss, Hair Fall and Alopecia

An aspect of this invention is directed to compositions, systems and methods for treating, ameliorating, and/or preventing "hair fall", i.e., hair loss, and/or stimulating hair growth in a person, patient or mammal. This invention relates to a method of minimizing or preventing undesirable hair fall from all over the skin or localized areas of the skin, including but not limited to the scalp, face, eyebrows, beard area, axillae, e.g., armpits, genital area and localized patches of bald hair (Alopecia) due to systemic or local causes and/or stimulating hair growth in such areas. The method of treatment for such hair fall comprises topically applying or administering to the area requiring such treatment a specific composition comprising, a mixture of sodium oxalate and oxalic acid in a specific stoichiometric ratio (percentage, by weight), and which may include a percentage of benzoic acid, salicylic acid and/or clobetasole, e.g., clobetasol propionate (a topical steroid) in a pharmacological composition comprising a pharmaceutical carrier.

The treatment of this invention is safe, effective and reduces and/or prevents hair loss and can stimulate hair growth in the treated area. Although not bound by such theory, it appears that repeated application activates a non-specific suppressor mechanism to suppress effector cells that are responsible for hair loss.

There are many hair loss conditions.

1) Alopecia Areata: Among the many factors which appear to be implicated in at least a proportion of such cases are the patient's genetic constitution, the atopic state, non-specific immune and organ specific autoimmune reactions and emotional stress. Characteristics are an initial lesion of a circumscribed total bald smooth patch 2) Trichotillomania: A compulsive habit which induces an individual to pluck his or her hair repeatedly. The result an ill-defined patch on which the hairs are twisted and broken at various distances from the clinically normal scalp. Much more unusual is the habit of excessively plucking the eyebrows and beard. The patient may pluck hair also or only from other region of the body such as pubis. These conditions commonly occur in neglected children and also in mentally retarded persons.

3) Brush Roller Alopecia: If brushing is applied frequently and with too much vigor this may cause irregular patches that appear like alopecia.

4) Hot comb alopecia: Typically women, usually black women, who use hot combs to straighten their hair may develop this type alopecia.

5) Massage Alopecia: The overenthusiastic application of medication to the scalp with massage may cause such baldness.

6) Alopecia secondary to hair weaving: Patchy traction alopecia has been reported to result from the cosmetic procedure of weaving.

The invention described herein provides an improved treatment method for hair loss that is effective, low cost, with minimal or no side effects using an easy to manufacture pharmacological composition for the treatment of hair fall and loss of hair and stimulating hair growth. The composition is applied to the areas of the skin, e.g., scalp, beard area and or other areas of the skin that have hair loss. The treatment can also be used for ameliorating, preventing and/or treating hair fall and hair loss diseases (Alopecia) and stimulating hair growth.

The method of this invention for treating hair fall and hair loss and/or stimulating hair growth comprises topically administering to a mammal a pharmacological composition, comprising a sodium oxalate and oxalic acid mixture with specific ratio by weight and percentage. A preferred composition for treating above mentioned conditions comprises a composition that includes a sodium oxalate and oxalic acid mixture with a specific stoichiometric ratio at 2.5% by weight in the topical composition that may have benzoic acid, salicylic acid and clobetasole.

EXAMPLE

Preparation of Active Composition of Sodium Oxalate and Oxalic Acid.

An equal amount by weight of a pharmaceutical grade sodium bicarbonate and oxalic acid are placed in a plastic container in a sterile open space at room temperature, i.e., 25° Celsius. The composition is mixed until a uniform mass is formed. A sufficient amount of purified sterile water is poured slowly into the container to allow the reaction of sodium bicarbonate and oxalic acid. The mixture is left for 24 hours to permit the water and carbon dioxide to evaporate and the mixture to dry. The mixture is then stirred again to permit the carbon dioxide and water vapors to further escape. Finally a white crystalline and odorless powder is obtained. The final product consists of 78.44% sodium oxalate and 21.56% Oxalic acid. The measured pH of the final product is 6. This solid product is now crushed and ground to a fine powder to produce the active composition, suitable for incorporation into a pharmaceutical carrier or vehicle.

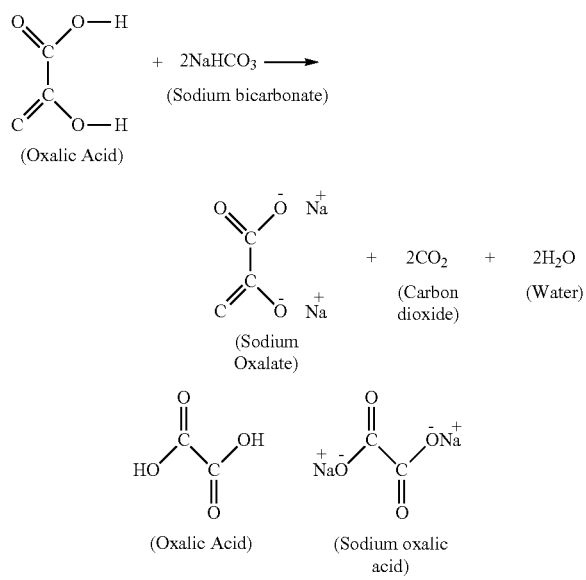

Preparation of Pharmacological Compositions

A. Preparation of Oil and Water Based Pharmaceutical Carrier or Vehicle ("Vehicle A") (1000 Grams on Small Scale):

1. Vessel A: Provide 750 grams of purified and sterile water in a suitable container, e.g., stainless steel vessel, and heat to about 70° Celsius.
2. Vessel B: Provide 250 grams of a pharmaceutical grade emulsifying wax and melt it by heating to 70° Celsius in a water bath.
3. Pour the heated water on Vessel A into Vessel B containing the emulsifying wax slowly and gradually, continue to stir to mix properly until wax and water become uniform and thickened, and temperature comes down to 35° Celsius, then let stand to cool. This water and oil base contains 25% emulsifying wax and 75% water by weight.

B. Addition of Active Composition, Benzoic Acid, Salicylic Acid and Clobetasole to Oil and Water Based Vehicle to Produce the Pharmacological Composition Used:

1. Preparation of the Pharmacological Composition for the Treatment of Alopecia ("Pharmacological Composition A")

A preferred pharmacological composition used for the treatment of alopecia consists of:
2.5% by weight of the active composition,
1.5% by weight of benzoic acid,
0.75% by weight of Salicylic Acid,
0.025% by weight of clobetasole
95.25% by weight of the oil and water based vehicle.

A preservative may be added as needed that maintains about the same ratios of ingredients and does not react with any ingredient of vehicle nor with any active composition.

2. Preparation of the Pharmacological Composition for the Treatment of Hair Fall ("Pharmacological Composition B")

A preferred pharmacological composition used for the treatment of hair fall consists of:
2.5% by weight of the active composition,
6.0% by weight of benzoic acid,
3.0% by weight of Salicylic Acid,
0.005% by weight of clobetasole
88.495% by weight of the oil and water based vehicle.

A preservative may be added as needed that maintains about the same ratios of ingredients and does not react with any ingredient of vehicle or with any active composition.

Method of Treatment

The pharmacological composition may be applied locally to the diseased or afflicted patients on the affected skin area of the scalp, face and or other skin areas that need to be treated. A therapeutically effective amount of pharmacological composition is applied to such skin area that will ameliorate, prevent and/or minimize hair fall and loss of hair and/or stimulate hair growth. Contact with the eyes with the pharmacological composition should be avoided.

Clinical Trials with Pharmacological Composition A

Patient: A
Age: 07
Gender: Male
Status: low socio-economic

History of complaints of Patient: Parents of child complains that his scalp was normal with erupted hairs one year back then all of a sudden gradually his hair were being lost and within one year it became a patch of hair loss within that period he also developed hair loss on back of the head. Patient got treatment from different doctors but there was no remarkable hair growth particularly on back of head.

Examination of patient: On examination of patient, there was a small patch of loss of hair on the center of scalp and also on occipital area there was big patch of Alopecia known ophiasis. There is poor prognosis in this condition. On examination of nails, there was pitting in 3 nails of fingers. After taking history from parent, Atopic condition lies in his family and on examination of patient after taking history case was diagnosed as atopic dermatitis. Laboratory investigation: IgE was high and complete blood picture showed eosinophilia. There was history of Bronchial asthma in his family.

Diagnosis: Alopecia Areata

Treatment and advice: Patient is given Pharmacological Composition A and advised to apply locally to the hair loss area, twice a day and advised to revisit after 15 days Patient 2$^{nd}$ Visit: Patient revisited 15 days after first visit to say that his hair has been regrown to a vast extent on scalp and on back of head. On examination of patient there was remarkable growth of hair on scalp patch and on occipital area patch. Patient is again given the same Pharmacological Composition A to apply in same manner and advised to revisit after 15 days.

Patient $3^{rd}$ visit: Patient revisited 15 days after the second visit, parents said that more hairs has been grown. On examination of patient remarkable growth of hair were observed on both patches. Patient was given the same Pharmacological Composition A to apply locally and also advised to revisit after 15 days.

Patient 4th visit: Patient came 15 days after the $3^{rd}$ visit with complete eruption of hair on both hair loss patches. Treatment was stopped. Patient was advised to revisit after 3 months.

Patient $5^{th}$ Visit: Patient revisited after 3 months of the last visit with same erupted hair.

Patient: B
Age: 21
Gender: Female
Status: Unmarried

History of complaints of Patient: Patient states that her elder sister suddenly noted a loss of hair on patient's scalp with round big patch. Patient did not see and know the length of time since she had developed this patch without hair.

Examination of patient: The patent had no history of previous diseases. On examination of patient there was a big patch of circumscribed bald area without hair. Additional investigations were performed, including CBC, Thyroid profile, RA factors. All investigations were normal.

DIAGNOSIS: Idiopathic Alopecia Areata

Treatment and advice: Patient is given Pharmacological Composition A and advised to apply locally twice a day. She is also advised to revisit after 15 days Patient $2^{nd}$ Visit: Patient visited 15 days after the first visit and said that more than 40% hair had erupted. On examination, there were some hair growth and more than 40% hair had grown on bald patch. Patient was given same Pharmacological Composition A to apply in same manner twice a day and advised to revisit after 15 days.

Patient $3^{rd}$ visit: Patient revisited 15 days after the previous visit with satisfaction. On Examination, it was found that more hair had grown. Patient was given the same Pharmacological Composition A & advised to revisit after 15 days.

Patient 4th visit: Patient visited 15 days after the previous visit. On examination of patient her bald area were fully covered with hair. Treatment was stopped. Patient was advised to revisit after 3 months.

Patient $5^{th}$ Visit: Patient revisited 3 months after previous visit to say that she is feeling slight baldness on scalp on same area. Patient was given Pharmacological Composition A to apply locally twice a day and advised if she feels further hair loss on bald area, she may revisit.

Patient: C
Age: 32
Gender: Male
Status: Married

History of Complaint of Patient: Patient complains of loss of hair over the past 3 months. Patient says that he first developed a small bald patch and gradually developed two more bald patches.

Examination of patient: On examination of patient, there were 3 small bald patches without hair. Patient does not have any history of systemic or local skin disease but he appears stressed. Additional investigations indicated there were no diseases, i.e., all was normal.

Diagnosis: Alopecia Areata due to emotional stress.

Treatment and advice: Patient is given Pharmacological Composition A to apply locally twice a day and revisit after 15 days Patient $2^{nd}$ Visit: Patient revisited 15 days after the first visit to say that there is no hair growth. On examination of patient, there seems no appearance of hair growth. The same Pharmacological Composition A was given to patient to apply twice a day and advised to revisit after 15 days.

Patient $3^{rd}$ visit: Patient revisited 15 days after the previous visit to say that his condition is same as it was. On examination of patient No hair growth observed. Same Pharmacological Composition A was given to patient to apply twice a day and advised to revisit after 15 days.

Patient 4th visit: Patient revisited 15 days after the previous visit to say that now some hair are growing. On examination of patient some hair were erupted at distance. Patient was given again the same Pharmacological Composition A to apply in same manner.

Patient $5^{th}$ Visit: Patient revisited 15 days after previous visit. On examination there was more hair growth. Patient was advised to revisit after 15 days. Patient was given same Pharmacological Composition A to apply in same manner and revisit after 15 days.

Patient $6^{th}$ visit: Patient came after 15 days of previous visit. On examination much more hair erupted and now the bald area appears to be somewhat covered. Patient again given same Pharmacological Composition A and advised to revisit after 1 month.

Patient $7^{th}$ visit: Patient revisited one month after previous visit to say there is slight more hair growth but not remarkable. On examination few more hairs are erupted. Patient given same Pharmacological Composition A to apply locally in same manner till the whole of the bald patches are covered with hair.

Patient: D
Age: 16
Gender: Female
Status: Unmarried

History of complaints of Patient: Patient complains of hair loss on eyebrows for the last 3 months. Patient said that she was alright 3 months before and then started shedding of hair gradually and within 3 months she lost half of eye brow hairs on both eyes. Patient did not have any history of systemic or local skin disease. Patient provided the genetic history of her father who also had developed hair loss.

Examination of patient: On examination of patient she had developed patches of hair loss on both eyebrows. Investigation did not reveal any hidden diseases.

Diagnosis: Genetically determined Alopecia Areata.

Treatment and advice: Patient is given Pharmacological Composition A to apply locally twice a day and advised to revisit after 15 days.

Patient $2^{nd}$ Visit: Patient revisited 15 days after the previous visit to say that some hair had been grown. On examination some hair had grown and patient was satisfied. Patient was given the same Pharmacological Composition A to apply locally in the same manner and advised to revisit after 15 days.

Patient $3^{rd}$ visit: Patient visited 15 days after previous visit with satisfaction. On examination of patient 75% hair had grown back and was covering the areas which had lost hair. The patient was give same Pharmacological Composition A to apply in the same manner and advised to revisit after 15 days.

Patient 4th visit: Patient revisited 15 days after the previous visit with full satisfaction. On examination of patients eyebrows the hair loss was completely restored and treatment was stopped. The patient was advised to revisit if she experienced hair loss.
Patient: E
Age: 42
Gender: male
Status: Married
History of complaints of Patient: Patient complained of hair loss on head and also on front of lower part of right leg. The patient complained that hair loss started about 4 months earlier. His head hair started shedding and gradually he acquired a big bald patch of hair on his head. Within the same period of time his front of right lower leg started gradually shedding hair. The patient had a big bald patch on his front of right lower leg.
Examination of patient: On examination of the skin of the patient, there were 2 big bald patches on his head and one on the front of his right lower leg. Investigation of patient did not reveal any diseases. Overall examination of the patient revealed him to be under emotional stress.
Diagnosis: Stress induced Alopecia Areata
Treatment and advice: Patient was advised to try and minimize his stress. Patient was given Pharmacological Composition A, to apply twice a day locally and revisit after 15 days.
Patient $2^{nd}$ Visit: Patient visited 15 days after first visit but there was only limited hair growth. Patient was given the same Pharmacological Composition A to apply twice a day in same manner and revisit after 15 days.
Patient $3^{rd}$ visit: Patient revisited 15 days after the previous visit with slight improvement and hair erupted more rapidly on effected area. Patient is given same Pharmacological Composition A to apply on both affected area in same manner and revisit after 15 days.
Patient 4th visit: Patient revisited 15 days after previous visit with good prognosis and more hairs had erupted. Patient given the same Pharmacological Composition A to apply in the same manner and revisit after 15 days
Patient $5^{th}$ Visit: Patient revisited 15 days after the previous visit with more improvement. More hairs had erupted on the patient. He was given the same Pharmacological Composition A to apply in the same manner and revisit after 15 days.
Patient $6^{th}$ visit: Patient revisited 15 days after previous visit with good hair growth. Additional hairs had erupted. The patient was given the same Pharmacological Composition A to apply in same manner and advised to revisit after 15 days.
Patient $7^{th}$ visit: Patient revisited 15 days after the previous visit. On examination of the patient full growth of hair had erupted and patient was satisfied. All treatment stopped.
Patient: F
Age: 40
Gender: Female
Status: married
History of complaints of Patient: Patient complained of loss of hair on front right side of scalp. Patient does not remember how long she had developed this area without hair. Her husband said that it had developed gradually over the past year.
Examination of patient: On examination of patient she had a big bald patch without hair growth on her head. In some places rudimentary hair was visible. After taking her detailed history, her husband said that their youngest son age 18 years had died in accident, Since that time she had stress and tension and was deliberately pulling her hair out.
Diagnosis: Traumatic Alopecia (Trichotillomania)
Treatment and advice: Patient was advised not to pull her hair. Her husband was directed to watch her. Patient was given Pharmacological Composition A to apply locally twice a day and revisit after 15 days.
Patient $2^{nd}$ Visit: Patient visited 15 days after previous visit with eruption of hair. Patient given same Pharmacological Composition A to apply locally twice a day in the same manner and revisit after 15 days. Patient's husband was again directed to watch her and try to prevent pulling hair out.
Patient $3^{rd}$ visit: Patient revisited after 15 days of previous visit with more hair growth and the bald area was covered with hair growth. The patient's husband was again directed to watch her and try to prevent pulling hair out. Patient was given the same Pharmacological Composition A to apply twice a day and revisit after 15 days.
Patient 4th visit: Patient revisited 15 days after previous visit with almost all hair grown back. Patient was given Pharmacological Composition A to apply in the same manner. Patient was advised to revisit after one month.
PATIENT $5^{TH}$ VISIT: Patient revisited one month after previous visit. On examination of patient all her bald patch areas were covered with hair. Treatment was stopped and patient's husband was directed to keep care of her as she should not pull her hair and better to consult psychiatrist for her mental condition as if she again pulls hair, she will again develop bald area.
Patient: G
Age: 12
Gender: Male student
Status: student
History of complaints of Patient: Patients parents brought a 12 year child with loss of hair on side of front scalp region that occurred over the past 1 year
Examination of patient: On examination of the patient there was loss of hair and a visible bald patch on frontoparietal area. After taking history from parents they said that he complained of nausea and vomiting. After thoroughly taking history of patient, parents said that he pulls out hair and eats the hair. They were also asked about his behavior and attitude. The parents said that he is slightly neglected as they give more attention and love to eldest son. The parents were told not to neglect him and divert his attention to keep him busy so that he would not pull out his hair and eat it.
Diagnosis: Traumatic Alopecia (Trichophagy)
Treatment and advice: Patient was given Pharmacological Composition A to apply twice a day and advised the parents to give more attention to him and keep care of him not to pull and eat the hair. Patient should be given biscuits and toffee and other items he liked. Patient was advised to revisit after 15 days.
Patient $2^{nd}$ Visit: Patient revisited 15 days after previous visit and examination at a distance indicated that some of the hair had erupted. Patient was given same Pharmacological Composition A to apply twice a day and the parents were directed to keep care and watch him.
Patient $3^{rd}$ visit: Patient revisited 15 days after previous visit with excellent improvement. Hairs had erupted nearer to each other. The patient was given the same Pharmacological Composition A and advised to apply in the same manner and revisit after 15 days.
Patient 4th visit: Patient revisited 15 days after previous visit with remarkable improvement. His bald patch was covered with hair with remarkable length of hair. Patient was given the same Pharmacological Composition A to apply in same manner and continue to apply furthermore for one month. Parents were directed to keep care of their child not to pull or eat the hair. Treatment is stopped.

Patient: H
Age: 30 years
Gender: Female
Status: Married
History of complaints of Patient: Patient complains of hair loss on the centre of scalp for last one year. Patient said that she began to shed her hair gradually over the past year. She tried different treatments but no beneficial results were obtained.
Examination of patient: On examination of patient, the center of the scalp acquired well demarcated big bald patch without hair with a dry rough scalp. After taking family history it revealed that her elder sister also developed the same bald patch. She also stated that her mother also had the same hair loss at about the same age.
Diagnosis: After taking full history, patient diagnosed as Androgenic Alopecica
Treatment and advice: Patient is given Pharmacological Composition A to apply locally twice a day and revisit after 15 days.
Patient $2^{nd}$ Visit: Patient visited 15 days after previous visit but there was no improvement at all. Patient is given same Pharmacological Composition A to apply twice a day and revisit after 15 days.
Patient $3^{rd}$ visit: Patient revisited 15 days after the previous visit but there was still no improvement and no eruption of hair. Patient given Pharmacological Composition A and advised to revisit after 15 days.
Patient 4th visit: Patient revisited 15 days after previous visit. On examination there appears to be 2 to 3 hairs erupting. Patient is given Pharmacological Composition A to apply locally twice a day and revisit after 1 month.
Patient $5^{th}$ Visit: Patient revisited 1 month after previous visit and examination of patient, there were only several hairs that had erupted. On examination 1 or 2 rudimentary hairs had erupted. Patient advised to revisit 1 month after previous visit.

In Androgenic Alopecia there was no rapid good result of treatment only one or two rudimentary hair are erupting at distances after two to three months. Patient was given same Pharmacological Composition A to apply in same manner and same way for prolonged period and time to time visit here when the Pharmacological Composition A is finished.
Placebo Control Study We selected our 3 diseased patients of Alopecia having different known pathology or idiopathic. We applied the simple vehicle based (Water and Oil based with emulsifying wax) and observeed the effects of given applied vehicle to apply locally.
TABLE A: Oil and purified water based vehicle (without incorporated pharmacological mixture)
Placebo Control Patient: A
Age: 25 YEARS
Gender: Female
Status: Married
History or complaints of Patient: Patient complained of hair loss of frontal area of skull for the past year.
Examination of patient: On examination of patient there was found a big patch of bald area. Patient said that for cosmetic purpose she frequently and vigorously used a roller. Her loss of hair was due to such use.
Diagnosis: Traumatic Alopecia
Treatment and advice: Patient was given Vehicle A and advised to apply a cream twice a day. And revisit after 15 days.
Patient $2^{nd}$ Visit: Patient revisited 15 days after the previous visit. There was no improvement at all, i.e., no hair growth.
Patient was given the same Vehicle A to apply twice a day and advised to revisit after 15 days.
Patient $3^{rd}$ visit: Patient revisited 15 days after previous visit. Upon examination of patient the bald patch remained the same. No hair growth at all. Patient is advised to revisit after 15 days.
Patient 4th visit: Patient revisited 15 days after the previous visit without having any hair eruption. On examination lesion was same as 2 months back. No application of vehicle A treatment stopped.
Placebo Control Patient: B
Age: 50
Gender: Male
Status: Married
History of complaints of Patient: Patient complain of Hair loss for the last 2 years which were gradually falling and acquired a big patch of Bald hair on center of scalp.
Examination of patient: On examination, Patient did not give any history of any systemic or local skin disease.
Diagnosis: Androgenic Alopecia
Treatment and advice: Patient is given Vehicle A to apply twice a day and revisit after 15 days
Patient $2^{nd}$ Visit: Patient revisited 15 days after the first visit. On examination of patient, there was no hair growth. Patient was given same Vehicle A to apply twice a day and revisit after 15 days.
Patient $3^{rd}$ visit: Patient revisited 15 days after the previous visit. The condition remained the same. Upon Examination of patient there was no hair growth. Patient was given same Vehicle A to apply twice a day and revisit after 15 days.
Patient 4th visit: Patient visited 15 days after the previous visit. There was no improvement.
Upon examination of patient his bald patch had not changed. There was no hair eruption at all. Treatment stopped.
Placebo Control Patient: C
Age: 8 years
Gender: male
Status: student
History of complaints of Patient: Patient's parents complained of bald spots on scalp at 2 areas, one on front of scalp, other on side of scalp that appeared over the last 6 months.
Examination of patient: The two small bald patches without hair were observed. Parents said that he had bronchial asthma.
Diagnosis: Alopecia Areata due to atopic dermatitis
Treatment and advice: Patient was given Vehicle A and instructed to apply twice a day and revisit after 15 days.
Patient $2^{nd}$ Visit: Patient revisited 15 days after previous visit without any improvement. Upon examination of patient, the lesions remained same.
Patient $3^{rd}$ visit: Patient revisited 15 days after previous date but on examination no improvement.

Lesion somewhat extended.
Patient 4th visit: Patient revisited 15 days after previous date without having any improvement, the lesion extended. Treatment is stopped as there is no improvement at all.
Clinical Trials with Pharmacological Composition B
Patient: A
Age: 50
Gender: female
Status: Married
History of complaints of Patient: Patient complains of hair fall over the last 2 months. Patient also says that her hair falls out with slight combing or using soap. Patient says that when she awakes in morning, hair appears on her pillow Examination of patient: On examination of patient she has very low density of hair by my touching hands on her hairs begins to fall. Patient is known case of breast cancer and she is on chemotherapy for the last two months.
Diagnosis: Hair fall due to chemotherapy
Treatment and advice: Patient given Pharmacological Composition B to apply to the scalp locally at night. Before applying the Pharmacological Composition B she is directed to moisturize her scalp and hair with cooking oil and water or otherwise with any hair conditioner. Patient is advised to revisit after 15 days
Patient $2^{nd}$ Visit: Patient revisited 15 days after the previous visit with slight improvement and hair erupted more rapidly on effected area. Patient was provided with Pharmacological Composition B to apply on both affected area in same manner and revisit after 15 days.
Patient $3^{rd}$ visit: Patient revisited 15 days after previous visit which good prognosis and more hairs were erupted. Patient was given Pharmacological Composition B to apply in same manner and advised to revisit after 15 days
Patient 4th visit: Patient revisited 15 days after the previous visit with more improvement. Further hairs were erupted patient was given Pharmacological Composition B to apply in same manner and revisit after 15 days.
Patient $5^{th}$ Visit: Patient revisited 15 days after previous visit with good hair growth. Additional hairs had erupted. Patient was given Pharmacological Composition B to apply in same manner and revisit after 15 days.
Patient $6^{th}$ visit: Patient revisited 15 days after previous visit. On examination of patient had full growth of hair and the patient was satisfied with the hair growth. All treatment stopped.
Patient: B
Age: 20
Gender: Male
Status: College student.
History of complaints of Patient: Patient complains of his hair fall from all over scalp over the last 3 month. Patient says that during combing, hair washing and even itself by touching hair and giving slight pulling his hair falls out.
Examination of patient: On examination of patient he has little density of hair on his scalp. After thorough checkup, e.g., blood CBC, Thyroid profile, RA Factor, etc. he appeared to be normal. He did not have any systemic or local disease.
Diagnosis: Idiopathic Hair fall.
Treatment and advice: Pharmacological Composition B was given to patient to apply at night locally. Before applying the composition the patient was directed to moisturize his scalp and hair either by cooking oil and water or any hair conditioner. He was also advised to wash his hair with suitable shampoo the next day. He was advised to revisit after 15 days.
Patient $2^{nd}$ Visit: Patient revisited 15 days after previous visit. Patient said that he had improvement and his hair falling had declined to some extent. Patient was told to repeat the same treatment with Pharmacological Composition B and revisit after 15 days.
Patient $3^{rd}$ visit: Patient revisited 15 days after previous visit and states that he has had greater improvement, i.e., less falling hair. Patient was told to repeat the same treatment with Pharmacological Composition B and revisit after 15 days.
Patient 4th visit: Patient revisited 15 days after previous visit and said he had 50% improvement in falling of hair, i.e., less hair fall. Patient was told to repeat the same treatment with Pharmacological Composition B and revisit after 15 days.
Patient $5^{th}$ Visit: Patient revisited 15 days after previous visit and said that he had a 75% improvement in falling of hair. Patient was told to repeat the same treatment with Pharmacological Composition B and revisit after 15 days.
Patient $6^{th}$ Visit: Patient revisited 15 days after previous visit to say that he has obtained a remarkable improvement and minimal hair fall. Treatment was stopped.
Patient: C
Age: 35 years
Gender: Female
Status: Married
History of complaints of Patient: Patient complained of her hair fall for the last 2 years. Patient said that her hair fall was too great. When combing, washing hair and even when she awakes in the morning she sees the hair on the pillow.
Examination of patient: Upon examination of patient, her scalp hair was of low density and was visible upon observation. Examination of patient, e.g., blood CBC, RA factor and thyroid profile, patient had Hypothyroidism and was using thyroxine medicine
Diagnosis: Hair fall due to Hypothyroidism.
Treatment and advice: Patient was given Pharmacological Composition B to apply on scalp at night. Patient was directed to apply cooking oil and water or any hair conditioner before applying Pharmacological Composition B and is advised to revisit after 15 days.
Patient $2^{nd}$ Visit: Patient revisited 15 days after the previous visit and observations indicated a slight improvement, although there was still hair fall. Patient was told to repeat the same treatment with Pharmacological Composition B and revisit after 15 days.
Patient $3^{rd}$ visit: Patient revisited 15 days after the previous visit and improvement was observed. Patient was told to repeat the same treatment with Pharmacological Composition B and revisit after 15 days.
Patient 4th visit: Patient revisited 15 days after the previous visit to say that she was getting remarkable improvement. Patient was told to repeat the same treatment with Pharmacological Composition B and revisit after 15 days.
Patient $5^{th}$ Visit: Patient revisited 15 days after the previous visit and patient say that she had 50% relief in hair falling. Patient was told to repeat the same treatment with Pharmacological Composition B and revisit after 15 days.
Patient $6^{th}$ Visit: Patient revisited 15 days after the previous visit and patient state that she had excellent improvement, but hair was still falling. Patient was told to repeat the same treatment with Pharmacological Composition B and revisit after 15 days.
Patient $7^{th}$ Visit: Patient revisited 15 days after the previous visit and patient stated that falling of hair has almost stopped, but a few hairs are still falling during combing and washing. Patient was told to repeat the same treatment with Pharmacological Composition B in same manner for 1 month more and after that stop the therapy.
Patient: D
Age: 10 years
Gender: male
Status: Student, low socioeconomic
History of complaints of Patient: Patient's mother complained of fall of hair from scalp of her child. She stated that he gets hair fall after combing, after taking a bath and even by touching and slight pressure on hair. Patient's mother complained of fall of hair for the last 8 months.
Examination of patient: On examination of patient, patient looks anemic. His CBC report show grossly anemic.

Diagnosis: Hair fall due to Anemia
Treatment and advice: Patient given Pharmacological Composition B to apply at night only and wash out next day. Patient is directed to apply oil and water or any hair conditioner on scalp and hair before applying Pharmacological Composition B. Patient's mother is also directed to feed him good balanced diet so that his anemic condition is corrected with the treatment and the child gets rapid benefit of treatment. Patient is advised to revisit after 15 days.
Patient $2^{nd}$ Visit. Patient revisited 15 days after the previous visit with slight improvement. Patient was told to repeat the same treatment with Pharmacological Composition B and revisit after 15 days.
Patient $3^{rd}$ visit: Patient revisited 15 days after the previous visit. There was an improvement. Patient was told to repeat the same treatment with Pharmacological Composition B and revisit after 15 days.
Patient 4th visit: Patient revisited 15 days after the previous visit. Patient had greater improvement in hair fall. Patient was told to repeat the same treatment with Pharmacological Composition B and revisit after 15 days.
Patient $5^{th}$ Visit: Patient revisited 15 days after the previous visit. Patient hair fall had improved remarkably. On examination of patient, his anemic condition also improved. Patient was told to repeat the same treatment with Pharmacological Composition B and revisit after 15 days.
Patient $6^{th}$ Visit: Patient revisited 15 days after the previous visit. Patient hair fall had vastly improved and only few hairs are falling during combing and washing. The hair shedding had stopped. Patient was told to repeat the same treatment with Pharmacological Composition B and revisit after 15 days.
Patient $7^{th}$ Visit: Patient revisited 15 days after the previous visit with remarkable improvement in hair fall. Treatment was stopped and the patient was directed to watch his Anemic condition and was provided with supplement diet instructions.
Patient: E
Age: 42 years
Gender: Female
Status: Married
History of complaints of Patient: Patient complained of her hair fall for the last 2 years. Patient stated that there was hair fall after combing, after washing and even with only slight traction of hair for binding with clip.
Examination of patient: On examination of patient she had low density of hairs. Most of the area of the scalp was devoid of hair. The patient's hairs appeared to be rough. After taking a complete history of the patient, she was not suffering from any systemic or local disease of the skin. The investigation included CBC, Thyroid profile, and RA factor. All was normal. She indicated that the relationship with her husband was not good. They quarreled and he was not a compromising person. She said that the tension was constant, i.e., "around the clock".
Diagnosis: Hair fall due to tension
Treatment and advice: She is given Pharmacological Composition B to apply only at night. Before applying Pharmacological Composition B she is instructed to, moisturize the scalp and hair with either Oil and water or with any hair conditioner and wash her hair next day. The patient is also advised to compromise with her husband and adopt a polite attitude to attract him so that she may get rid of tension. Patient was requested to revisit after 15 days.
Patient $2^{nd}$ Visit: Patient revisited 15 days after the previous visit with slight improvement. Patient was told to repeat the same treatment with Pharmacological Composition B and revisit after 15 days.
Patient $3^{rd}$ visit: Patient revisited 15 days after the previous visit with further improvement in her hair fall as she stated. Patient was told to repeat the same treatment with Pharmacological Composition B and revisit after 15 days.
Patient 4th visit: Patient revisited 15 days after the previous visit patient and stated that she had excellent improvement in her hair fall. Patient was told to repeat the same treatment with Pharmacological Composition B and revisit after 15 days.
Patient $5^{th}$ Visit: Patient revisited 15 days after the previous visit. Now patient states that she has got remarkable improvement in hair fall. Patient was repeated same REMEDY and advised to use it in same manner as it was told previously and revisit after 15 days.
Patient $6^{th}$ Visit: Patient revisited 15 days after the previous visit. She had full satisfaction and there was a remarkable improvement in her hair fall, She had only a few hairs fall during her application of pressure from combing and washing. Patient was told to repeat the same treatment with Pharmacological Composition B and revisit after 15 days.
Patient $7^{th}$ Visit: the patient revisited 15 days after the previous visit to state that there was excellent improvement and only few hair sometimes fall. Treatment stopped but patient is again advised and directed to compromise with her husband and keep your marital life happy because if you again remain in stress and tension, the hair may again begin to fall.
Patient: F
Age: 16 years
Gender: Female
Status: college student
History of complaints of Patient: Patient complained of hair fall for the last 3 years. Patient stated that any slight force applied on hair, e.g., combing or washing hair, the hair begins to fall. She also complained that even without applying any pressure to the hair, it would fall out. When she awoke in the morning, her pillow had fallen hair.
Examination of patient: Her fingers appeared to be swollen. She also complained of Joints pain for the last 3 years according to statement of patient. She has Rheumatoid arthritis and is on anti-Rheumatoid arthritis medicine. Further examination confirmed that she is suffering from RA.
Diagnosis: Hair fall due to Rheumatoid Arthritis
Treatment and advice: Patient given Pharmacological Composition B to apply at night and advised to wash her hair the next day. Patient was directed to moisturize her hair either with cooking oil and water or any hair condition. Patient was advised to revisit after 15 days.
Patient $2^{nd}$ Visit: Patient revisited 15 days after the previous visit with slight improvement. Patient was told to repeat the same treatment with Pharmacological Composition B and revisit after 15 days.
Patient $3^{rd}$ Visit: Patient revisited 15 days after the previous visit with slight more improvement. Patient was told to repeat the same treatment with Pharmacological Composition B and revisit after 15 days.
Patient 4th visit: Patient revisited 15 days after the previous visit with good improvement and the fall of hair has been stopped to a great extent. Patient was told to repeat the same treatment with Pharmacological Composition B and revisit after 15 days.

Patient 5th Visit: Patient revisited 15 days after the previous visit with more improvement. Patient was told to repeat the same treatment with Pharmacological Composition B and revisit after 15 days.

Patient 6th Visit: Patient revisited 15 days after the previous visit with excellent improvement and said that hairs are still falling but not too much and very few are falling. Patient was told to repeat the same treatment with Pharmacological Composition B and revisit after 15 days.

Patient 7th Visit: Patient revisited 15 days after the previous visit to state that she has remarkable improvement with the stoppage of hair fall and only few hairs as normally falls are falling. Treatment is stopped and patient is advised to continue to take her medicine for Rheumatoid Arthritis.

Placebo Control Study

We selected 3 patients having hair fall but different known pathology or idiopathic. We applied Vehicle A consisting of an oil and water based mentioned below without any active ingredients of our pharmacological composition. The patients were not told that this was a placebo Vehicle A, but told them it was a treatment composition for their hair fall.

Patient: A
Age: 35 yrs
Gender: Male
Status: Married
History of complaints of Patient: Patient complained of hair fall from his scalp for the last 2 years. He says that his hair fall occurred after combing his hair and washing and even without any pressure on his hair. This occurred over the past 2 years. Patient says that he received treatment from different doctors but he could not obtain relief.
Examination of patient: Upon examination of patient and after taking his history, patient was healthy and not suffering from any systemic or local illness.
Diagnosis: Idiopathic Hair fall.
Treatment and advice: Patient is given Vehicle A to apply at night only. Before applying the vehicle, he is advised to wash his hair the next day and advised to revisit after 15 days.

Patient 2nd Visit: Patient revisited 15 days after the previous visit. Patient stated that there is no improvement at all. Hairs were falling at the same rate as previously observed. Patient was told to repeat the same treatment with Vehicle A and revisit after 15 days.

Patient 3rd visit: Patient revisited 15 days after the previous visit disheartened and indicating the treatment is not effective. He asked to change the treatment. Patient was told to repeat the same treatment with Vehicle A and revisit after 15 days.

Patient 4th visit: Patient revisited 15 days after the previous visit. He was very irritated to say I am not getting improvement at all. Thank you for your treatment I will change my doctor.

Patient: B
Age: 18 years
Gender: Female
Status: student, unmarried
History of complaints of Patient: Patient complained of hair fall for the last 2 years. She said that as she combed her hair, washed her hair or gave a slight traction to hair, her hair fell out.
Examination of patient: Upon examination of the patient and taking history of patient she had Juvenile Rheumatoid Arthritis
Diagnosis: Juvenile Rheumatoid Arthritis
Treatment and advice: Patient is given Vehicle A to apply at night only. Before applying Vehicle A she should moisturize her hair with either cooking oil and water or with hair conditioner and wash her hair next day with any suitable shampoo. Patient is advised to revisit after 15 days.

Patient 2nd Visit: Patient revisited 15 days after the previous visit to say that there appears no improvement at all. Patient was told to repeat the same treatment with Vehicle A and revisit after 15 days.

Patient 3rd visit: Patient revisited 15 days after the previous visit to say that she is not satisfied with the treatment. Patient did not want to continue treatment. Patient was told to repeat the same treatment with Vehicle A and revisit after 15 days.

Patient 4th visit: Patient revisited 15 days after the previous visit with very irritable mood to say that she was not getting improvement at all and withdrew from treatment.

Patient: C
Age: 50 years
Gender: male
Status: married
History of complaints of Patient: Patient complained of hair loss for a long time. He complained that his hair falls by itself and there was increased hair fall on combing and washing.
Examination of patient: After taking his history, patient is a diabetic and is on anti-diabetic medicine.
Diagnosis: Hair fall probably due to his medicines and diabetes.
Treatment and advice: Patient was given Vehicle A to apply at night and wash it next day by any suitable shampoo. Patient was advised to take care of his diabetic condition and keep it under control. Patient was told to treat with Vehicle A and revisit after 15 days.

Patient 2nd Visit: Patient revisited 15 days after the previous visit to say that there is no improvement at all. Patient was told to repeat the same treatment with Vehicle A and revisit after 15 days.

Patient 3rd visit: Patient revisited 15 days after the previous visit to say that still there is no improvement. Patient was told to repeat the same treatment with Vehicle A and revisit after 15 days.

Patient 4th visit: Patient revisited 15 days after the previous visit to say I he was not getting any improvement at all. Patient was told to repeat the same treatment with Vehicle A and revisit after 15 days.

Patient 5th Visit: Patient did not attend scheduled appointment.

Treatment and Prevention of Lice

Clinical Trials and Data for the Treatment of Lice in Mammals

Preparation of Pharmacological Composition and Carrier.
Some specific examples of embodiments of the pharmacological composition and the carriers therefore.
Preparation of Oil and Water Based Vehicle (1000 Grams on Small Scale):
Vessel (a)—Take 750 grams of purified and sterile water is placed in a suitable container, e.g., a stainless steel vessel and heated to about 70 Degrees Celsius.
Vessel (b)—Take 250 gram of emulsifying wax (pharmaceutical grade) and melt it by heating up to about 70 Degrees Celsius in a water bath.
Pour water into Vessel (b) containing the emulsifying wax slowly and gradually, continue to stir to mix properly until wax and water become uniform and thickened, and temperature decreases to about 35 Degrees Celsius, then let it cool.

The content of the two vessels are mixed to prepare a composition containing (by weight) 25% emulsifying wax and 75% water ("pharmaceutical carrier")

Preparation of Final Remedy to Apply Locally

To prepare the pharmacological composition that is used in the method of this invention for the treatment of lice, to apply topically to the area infected with lice, incorporate about 5% of the active composition by weight and about 0.025% $KMnO_4$ (potassium permanganate) by weight into the above pharmaceutical carrier.

Clinical Trial

Patient: 1

Age: 07

Gender: Male

Status: low socio-economic

History of Complaints of Patient:

Parents of child complained that he was alright 1 year previous to visit. Complaints gradually increased about scalp itching. When scalp was inspected there were big and small lice crawling on scalp and on hair. Mother of patient also complained that after combing the hair there was shedding of many live large and small lice.

Examination of Patient:

Upon examination of patient, there were nits, nymph and lice crawling on scalp and hair and due to the crawling of lice and nymph, patient had developed itching. Patient also complained that he itches his scalp and wakes up from sleep at night on and off due to the itching during his sleep period Diagnosis: Pediculosis Treatment and Advice:

Patient was given the pharmacological composition of this invention which was applied at night to the scalp and combed to remove the lice. The ratio of dead to alive lice 12 hrs after combing was observed. The patient was also advised to wash his hair after 12 hrs of application of medicine and revisit the physician after 10 days Patient 2nd Visit:

Patient revisited after 10 days, his parents were happy to say that their son obtained relief and now he can sleep deeply at night and there are a minimal number of lice on his scalp. Upon examination, there were only a minimum amount of nymph and lice crawling and a few nits were attached to the hair. The patient was again given the pharmacological composition of this invention and advised to apply at night to the scalp and combed to remove the lice. He was advised to revisit after 10 days.

Patient 3rd visit:

Patient revisited 10 days after the previous second visit. The parents indicated that he now had complete relief and there were no more lice or nymph on his scalp and also he was sleeping deeply without having to itch his scalp. However, attached nits were still visible. Patient was given the same pharmacological composition of this invention and directed to apply it at daily at night to the scalp and then comb to remove the lice until the hair becomes clear of lice.

Patient: 2

Age: 21

Gender: Female

Status: Unmarried, low socioeconomic and unable to read and write

History of Present Complaints:

Patient states that whenever she combs hair, a lot of big and small lice are shed. She also complains that she has developed wounds on her scalp and some of the wounds have pus in it. Whenever she combs hair, she gets pain and irritation. Particularly at night there is a lot of itching which does not allow her to sleep. She remains sleepless at night.

On Examination of Patient:

Upon examination of the patient, she appeared to be anemic, her scalp and hairs had a lot of nits, nymphs and lice. Upon examination of the scalp and hair, she had many wounds on the scalp which indicated that she was infected with pediculosis.

DIAGNOSIS: pediculosis

Investigation:

Patient is directed for Lab test of CBC & wounds pus culture for sensitivity and advised to revisit after doing investigation and report.

Patients 2nd Visit:

Patient visited 7 days after the first visit with Investigation report. The report showed anemia and the pus culture report showed growth of bacteria, it means there were secondary bacterial infection superseded after the pediculosis. The patient was given an antibiotic to eradicate the superseded bacterial infection and also given vitamins and advised the patient to have a nourishing diet to avoid her anemic condition. She was also advised to comb twice daily to remove the lice as much as she can so that she can get relief before starting of proper treatment against the lice, i.e., treatment with the pharmacological composition of this invention, as lice treatment cannot be given in the presence of wounds. Patient was advised to revisit after 7 days.

Patient 3rd Visit:

Patient visited 7 days after her previous visit. Her wounds were cured and she had some relief. Upon examination of the patient, her wounds had declined and cured. However, the nits, nymph and lice still occupied her scalp.

Treatment and Advice:

Now the patient is given the pharmacological composition of this invention for the treatment of lice. She was directed to apply the composition locally to her scalp at night and advised to comb after 12 hours and inform the doctor in the next visit how many dead lice and nymph have been shed. Patient was advised to revisit after 10 days.

Patient 4th Visit:

The patient revisited 10 days after the previous visit to say that she had obtained substantial relief She combed her hair 12 hours after application of the pharmacological composition. There were many dead lice shedding among, only about 5% shed lice were alive and 95% were dead.

upon examination of the patient most of her hair and scalp were free of lice, nymph and nits. Patient was given the same the pharmacological composition and was advised to repeat the treatment and return for a check up in 10 days.

Patient 5th visit:

Patient revisited 10 days after previous visit and was pleased in that she had a lot relief from the lice and she can sleep without pain and itching. She hardly had any lice or nymph appears. Her lice appeared to have been has been eradicated. Upon examination, the patient's scalp and hair were free from lice and nymph and had the normal texture of hair in look and feel and was devoid of lice and nymph. However, there were some nits visible that were cemented to the hairs by a chitinous material. The patient was directed to continue the same treatment mode until the attachment of nits are removed as the pharmacological composition liquefies the chitinous material and the nits are detached from the hairs and easily removed with combing to make the hair clear, neat and clean.

Patient: 3

Age: 65

Gender: Male

Status: Married

History or Complaints of Patient:

Patient complained of Lice on hair. Patient also complained of something crawling on his scalp which causes disturbance in sleep.

Upon Examination of Patients:

Upon examination of patient, his scalp and hair had nits, nymph and lice. Patient appears to be a depressed and neglected. On taking history of patient, Patient told that his wife and son have left him alone and he is living in a small place in dorm. No one is caring and looking after him. He is helped by random persons. One of the persons, who works in the dorm brought him to the doctor for treatment.

Diagnosis: Pediculosis

Treatment and Advice:

He was given the pharmacological composition and told to apply it at night regularly to the scalp and hair for the treatment of lice, to comb the hair after 12 hrs and wash the scalp and hair. Patient was told to do this treatment and wash hair daily and advised to revisit after 10 days.

Patient 2nd Visit:

The patient was brought to the doctor by the same attendant 13 days after the previous visit. Upon examination, there were many dead lice found on the hair and scalp. After taking the history from the attendant and from the patient, it indicated that he was just applying the medicine on scalp but not washing or combing his hair. A bad smell was coming from his scalp. There is no one to care for him. He was simply applying the pharmacological composition regularly every night but not washing his hair.

I advised him to get services from nursing staff to comb his hair. He combed his hair in front of the physician and there were many dead lice shed. But even then some of the hair and scalp had lice, nymph and nits. He was again given the pharmacological composition to apply to his scalp and the physician requested his nursing staff to visit the patient daily to comb his hair. The same service remained continued for 1 month.

Patient 3rd visit:

After 1 month the patient returned, his scalp was clear from lice. The patient was advised to visit the physician if he developed lice again.

Patient: 4

Age: 05

Gender: female

Status: low socio economic

History of Complaints of Patient:

Mother of patient complained that her child had developed lice on her scalp hair which caused itching and woke her up in the evening.

Examination of Patient:

Upon examination of the patient the scalp and hair had numerous nits, nymphs and lice.

Diagnosis: Pediculosis capitis

Treatment and Advice:

The patient was given the pharmacological composition for the treatment of lice, nits and nymph and instructed to apply it locally on her hair and scalp every night and comb her hair and wash it after 12 hours and also observe the number of dead and live lice, nymphs and nits. The patient was advised to revisit after 10 days.

Patient 2nd Visit:

The patient revisited after 10 days, completely satisfied in that the scalp and hair had become clear and there were no more nymphs and lice on the scalp. The patient was given the same remedy to apply once a week locally just to prevent the reappearance of the lice.

Patient: 5

Age: 75

Gender: Female

Status: Married

History or Complaints of Patient:

Patient was brought to physician by her family members who observed lots of lice. The patient's family indicated that she is generally neat and clean but in spite this care she still develops lice on her scalp and hair.

Upon Examination of Patient:

Upon examination of the patient, she appeared to come from a very respectable family and cared for by her family members. She bathes regularly. The physician examined her hair and scalp and there were nits, nymphs and lice on her scalp.

Diagnosis: Pediculosis

Treatment and Advice:

The patient was given the pharmacological composition to apply daily on the scalp and hair at night and wash her hair after 12 hours of application. The patient was also advised to return to the physician after 10 days.

Patient 2nd Visit:

The patient revisited after 10 days and the family members and the patient were very happy and thankful as all her lice and nymph were dead and most of the nits were removed but still some of the nits remain attached and visible. Upon observation, the patient's scalp were clear and free from lice indicating that the pharmacological composition was effective. As some of the nits wre still attached to the hair, the patient was advised to apply the same remedy in same manner and revisit after 10 days.

Patient 3rd visit:

The patient revisited after 10 days with complete satisfaction and complete relief without having itching, irritation, restlessness. Patient was also sleeping comfortably. After examination of scalp of patient, there were no visible lice and nymph and most of the nits are removed but at some places nits were visible so. The pharmacological composition was given to the patient and she was told apply it once a week. All the nits should be completely removed by then.

Patient: 6

Visit by physician to "Low Socio-economic" institution for children

History of Complaints of Patients:

The physician was called to check and treat children below 12 years of age in a very low socio-economical institution where children are taught collectively, seated shoulder to shoulder on the floor. The head of the institution briefed physician and stated that most of the students appeared to be infested by the lice. During the inspection, they scratched their scalps and during the cleaning of the facilities the complaint was that lice were crawling over floor.

On Examination of Patients:

Upon examination of the students it was found that most of the children had nits, nymph and lice on their scalp and some of the students had wounds on their scalp due to the lice which created an environment for a bacterial infection. Upon inquiry of some of the children they complained of itching, restlessness and sleeplessness at night due to crawling of lice.

Diagnosis—Pediculosis

Treatment and Advice:

The patients were treated according to observations and symptoms. Patients were divided into 2 groups.

Group A, include patients who complained of itching, irritation, sleeplessness and lice on scalp and hair but no wounds or lesions on scalp.

Group B, is included patients who have developed superseded bacterial infection with wounds and lesions.

In Group A, the pharmacological composition was given for the treatment of the lice to apply locally and wash the hair and scalp 12 hours after treatment of application regularly.

Group B, the wound and lesion (occurred due to the superseded bacterial infection after itching caused by lice) was first treated by an oral and topical application of an anti-biotic to first combat the bacterial infection. The patients were then advised to use the pharmacological composition as per instruction for 10 days until the physician's next visit. as my next visit will be after 10 days.

2nd Visit:

The physician visited 10 days latter to check the treated cases. Both the groups benefited from the treatments.

In group A, after combing many dead lice were shed and there was a declination of density of lice, although some of the lice were preset on scalp.

In group B, the wounds and lesions were settled, and the patients started to apply the pharmacological composition daily at night and to comb and wash the hair after 12 hours and requested to observe how many dead and alive lice were shedding.

Both groups of patients were advised that the next visit would be in 10 days.

3rd visit:

The physician visited after 10 days and the head of institution was satisfied and very happy just to see the children that there was a remarkable declination of occupied density of lice on hair and scalp of both groups of patients. The drugs were given to head of the institution with the instruction to apply the medicine the same way as previously instructed for another 10 days and afterwards just to apply as preventive measure weekly to combat the development of lice.

Patient: 7
Age: 27
Gender: Male
Status: Unprotected sexual intercourse with sex worker
History of Complaints of Patient:
Patient complains of itching, irritation and crawling of something on genitals and axillary area for the last 15 days.
On Examination of Patients:

Upon examination of whole hairy area of the skin including scalp, eyelashes, beard, axillae and pubic hairs of patient, only the pubic and axillary hairs were occupied with crab lice attached to hairs. The crab lice were found only on pubic hair and axillae. It indicated that he had some sexual contact with the infested person suffering from the phthiriasis pubis. After taking the detail history of sexual contact, patient said that he was involved in sexual contact with sex worker.

Diagnosis: Phthiriasis pubis (crab lice).
Treatment and Advice:

Patient was given the pharmacological composition to apply locally once a day for 10 days on all hairy areas except scalp and body as the crab lice cannot hold scalp and body hairs and was directed to observe the movement of lice on those attached lice area after 12 hours and observe how many lice movement are alive and appear to move and advised to revisit after 10 days.

Patient 2nd Visit:

The patient revisited after 10 days. He was completely cured and did not complain of crawling or movement of lice nor did he complain itching, however there was some irritation. The patient was again given the pharmacological composition to continue due to the observation that nits are attached to the hair and the pharmacological composition will liquefy the chitinous material by which nits attach to hairs and break the life cycle of the lice by detaching the nits and killing the nymph and lice. The patient was also advised to comb the affected area twice a day and avoid having sexual contact with infected partners.

Patient: 8
Adult domestic Dog
History or Complaints:

The owner of the domestic dog came to physician with complaint that his domestic dog has developed lice over his hairs and the dog appears to be restless, losing weight, irritable and does not sleep. Whenever he pats the dog he observes lice over its skin as well as multiple abrasion marks due to the rubbing and licking by dog. He used the fipronil— a known flea and tick treatment—multiple times but his dog were not getting better.

Diagnosis: Pediculosis
Treatment and Advice:

The owner of dog was given the pharmacological composition to apply daily at the night all over the hairy skin and brush the hairs and observe the number of shed dead and alive lice. Additionally, bathe the dog after every of application of medicine 12 hours later. Owner was advised to report progress after 10 days.

Dog Owner 2nd Visit:

The owner of the dog visited after 10 days to say that the lice of the dog had declined dramatically and 75% of the skin/fur area was clear of lice. Whenever he brushed hair, among them 90% shed lice were dead while only 10% appear to be alive with sluggish movement.

The same was repeated and advised to apply in same way as previously and report to me after 10 days.

Dog Owner 3rd Visit:

The owner of dog revisited after 10 days with full satisfaction. Owner informed me that he already stopped the medicine as his loving dog skin and hairs become free from lice and also all the itching, irritation and sleeplessness were subsided.

Patient: 9
Age: 08
Gender: female
Status: low socioeconomic and mother is dead, no one in family to look after and proper care.
History of Complaints of Patient:

Father of girl brought his daughter with the complaint of irritation and rubbing on eyelids and pulling of eyelashes for the last 4 months. Patient's father says that she got treatment from different places but neither any relief nor got any diagnosis. Father complained that she remained restless and rubbed her eyelids, but couldn't find out the cause of irritation and rubbing by his daughter. He believed that something was in her eyelashes. He consulted an ophthalmologist who then referred the case to a dermatologist. The ophthalmologist informed him that his daughter has nothing wrong inside her eyes.

Upon Examination of Patients:

Upon taking the history and examining the patient, it was revealed that as her mother is dead and no family member to take interest in taking care of her. She passes most of her time outside the home on the street with other children. Due to the carelessness and non-caring of child, patient got crab lice from somewhere and the population of lice is continuously increasing. Upon examination of all her hair and skin, including scalp hair, eyebrows, eyelashes, axillary and pubic area were clear. Only the eyelash hairs had lice.

Microscopic Examination:

Upon microscopic examination of one of the louse on the eyelash it was revealed that it was the sub order group of *Pthirus pubis*.

Diagnosis—Crab lice.

Treatment and Advice:

The patient was given the pharmacological composition to apply on the eyelashes daily at night and also advised to apply simply on eyelashes as it should not come in contact within the eye as it will cause irritation. After 10 hours remove it very slowly with tissue paper. Patient father was advised to revisit after 10 days.

Patient 2nd Visit:

The patient revisited after 10 days. The patient's lice are immovable indicating that they are dead while only few of them shows movement indicating that they are alive. The physician removed the dead lice with care by tweezers. Before removing the dead lice an emollient was applied to loosen the grip of lice. The patient was again given the pharmacological composition to apply in the same manner and advised to revisit every 5 days so that the physician can remove all the attached lice without pain or irritation.

Patient 3rd visit:

The patient revisited after 5 days to say that there appears no movement in the lice. The physician removed all the attached lice with tweezers to make her eyelashes clear from the harbor of lice on eyelashes and again given the same medicine to patient to apply weekly for 1 month to combat the environmental condition for the development of lice.

Patient: 10

Status: Cattle farm

History of Complaints:

The cattle farm house has buffalos, cows and goats etc. The owner of the cattle farm came to physician to state that most of his cattle including buffalos, cows and goats have lice on their whole body due to this fact that most of his animals remain restless and rub their skin by rubbing on the ground and walls due to itching because they have lice on their hairs and skin. The veterinarian could not get relief for his animals. The owner of the cattle was given the pharmacological composition for the treatment of lice and advised the owner to apply all over the body at night and wash them after 12 hours of application and inform the physician of the results after 10 days.

Owner Visit:

The owner visited after 10 days and said that his cattle are getting relief and the lice are dieing. Irritations and restlessness of the cattle declined. This medicine is highly effective for cattle. He also requested the physician to give the pharmacological composition to him in mass quantity just to apply over the whole body of his cattle as on regular basis for few days and weekly after eradication of lice.

While various changes may be made in the detailed compositions and processes of this invention, it will be understood that such changes will be within the spirit and scope of the present invention. Having thus described the invention in detail, it is to be understood that the foregoing description is not intended to limit the spirit and scope thereof. What is desired to be protected by Letters Patent is set forth in the appended claims.

What is claimed:

1. A method of treating a lice infection in a mammal having such lice infection in a specific area of skin and hair of the mammal, comprising:
   topically applying to the specific area of the skin and hair a therapeutically effective amount of a pharmacological composition to kill the lice and dislodge them from the mammal skin and hair, comprising:
   a pharmaceutical carrier;
   an active composition consisting of an amount of about 2% to 10% a mixture of sodium oxalate and oxalic acid;
   wherein the pharmacological composition is safe and effective for the treatment of lice in the mammal.

2. A method of treating a lice infection in a person having such lice infection in a specific area of skin and hair of the person, comprising:
   topically applying to the specific area of the skin and hair a therapeutically effective amount of a pharmacological composition to kill the lice and dislodge them from the skin and hair, comprising:
   a pharmaceutical carrier;
   an active composition consisting, of an amount, of about 2% to 10% a mixture of sodium oxalate and oxalic acid;
   wherein the pharmacological composition is safe and effective for the treatment of lice in the mammal in the specific area of the skin.

3. A method of treating a lice, nit and nymph infection in a person having such lice, nit and nymph infection in a specific area of skin and hair of the person, comprising:
   topically applying to the specific area of the skin and hair a therapeutically effective amount of a pharmacological composition to kill and dislodge the lice, nit and nymph from the skin and hair, comprising:
   a pharmaceutical carrier;
   an active composition consisting of an amount of about 2% to 10% a mixture of sodium oxalate and oxalic acid;
   wherein the pharmacological composition is safe and effective for the treatment of lice, nit and nymph infection in the person.

4. The method of claim 2, wherein the mixture of sodium oxalate and oxalic further includes about 0.025% by weight of $KMnO_4$.

5. The method of claim 2, wherein the mixture of sodium oxalate and oxalic acid is about 73% to about 83% sodium oxalate and about 17% to about 27% oxalic acid.

6. The method of claim 2, wherein the mixture of sodium oxalate and oxalic acid is about 78.44% of Sodium oxalate and about 21.56% oxalic acid.

7. The method of claim 2, wherein the pharmaceutical carrier is a composition consisting of an oil and water based vehicle.

8. The method of claim 2, wherein the pharmacological composition consists of about 0.03% to about 15% of the active composition.

9. The method of claim 7, wherein the pharmacological composition consists of 5% by weight of the active composition.

10. The method of claim 2, wherein the pharmacological composition is applied at least once a day to the specific area of the skin.

* * * * *